(12) United States Patent
Koide

(10) Patent No.: US 11,987,595 B2
(45) Date of Patent: May 21, 2024

(54) FLUOROGENIC PROBE USING A MISLOW-EVANS REARRANGEMENT FOR REAL-TIME IMAGING OF HYDROGEN PEROXIDE

(71) Applicant: University of Pittsburgh—Of the Commonwealth System of Higher Education, Pittsburgh, PA (US)

(72) Inventor: Kazunori Koide, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 113 days.

(21) Appl. No.: 17/514,356

(22) Filed: Oct. 29, 2021

(65) Prior Publication Data

US 2022/0135604 A1 May 5, 2022

Related U.S. Application Data

(60) Provisional application No. 63/107,733, filed on Oct. 30, 2020.

(51) Int. Cl.
| | | |
|---|---|---|
| *C07F 11/00* | (2006.01) | |
| *G01N 1/30* | (2006.01) | |
| *G01N 21/64* | (2006.01) | |
| *G01N 33/84* | (2006.01) | |

(52) U.S. Cl.
CPC ............ *C07F 11/00* (2013.01); *G01N 21/643* (2013.01); *G01N 33/84* (2013.01); *G01N 2021/6439* (2013.01)

(58) Field of Classification Search
CPC ....... C07F 11/00; G01N 21/643; G01N 33/84; G01N 2021/6439; G01N 1/30
See application file for complete search history.

(56) References Cited

PUBLICATIONS

Pham et al., 2020, Angewandte Chemie, 59, 17435-17441.*
RN 2418023-19-3, Jun. 3, 2020, registry database compound.*
RN2478516-66-2, registry database compound, Sep. 11, 2020.*
Bickart et al., "The Thermal Racemization of Allylic Sulfoxides and the Interconversion of Allylic Sulfoxides and Sulfenates, Mechanism and Stereochemistry", Journal of the American Chemical Society, Aug. 28, 1968, pp. 4869-4876, vol. 90:18, Department of Chemistry, Princeton University.
Evans et al., "Allylic Sulfoxides: Useful Intermediates in Organic Synthesis", Accounts of Chemical Research, 1974, pp. 147-155, vol. 7, Department of Chemistry, University of California.
Pham et al., "Fluorogenic Probe Using a Mislow-Evans Rearrangement for Real-Time Imaging of Hydrogen Peroxide", Angew. Chem. Int., 2020, pp. 17435-17441, vol. 59, Wiley-VCH GmbH.
Reich, "Synthesis and Stereochemistry of (±)-3',4'-Dihydrousambarensine", J. Org. Chem., 1975, pp. 2570-2572, vol. 40, No. 17, Department of Chemistry, University of Wisconsin.

* cited by examiner

*Primary Examiner* — Sun Jae Yoo
(74) *Attorney, Agent, or Firm* — The Webb Law Firm

(57) ABSTRACT

Provided herein is a fluorogenic probe that selectively undergoes a [2,3]-sigmatropic rearrangement (seleno-Mislow-Evans rearrangement) with $H_2O_2$, followed by an acetal hydrolysis, to produce a green fluorescent molecule in seconds. Also provided herein is a method of identifying or visualizing the presence of $H_2O_2$ in a cell, tissue, organ, or organism that includes contacting the cell, tissue, organ, or organism with the fluorogenic probe. Also provided herein is a method of identifying or quantifying the presence of $H_2O_2$ in a sample that includes adding to or mixing in the sample the fluorogenic probe.

19 Claims, 31 Drawing Sheets
(5 of 31 Drawing Sheet(s) Filed in Color)

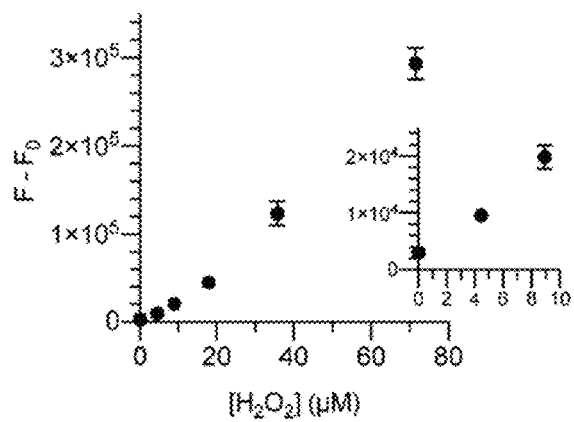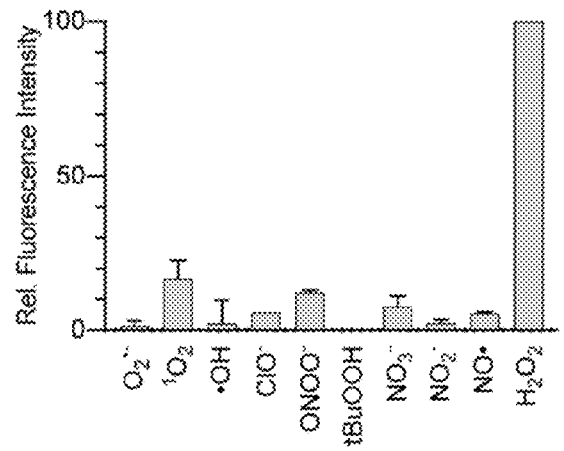
FIG. 14A
FIG. 14B
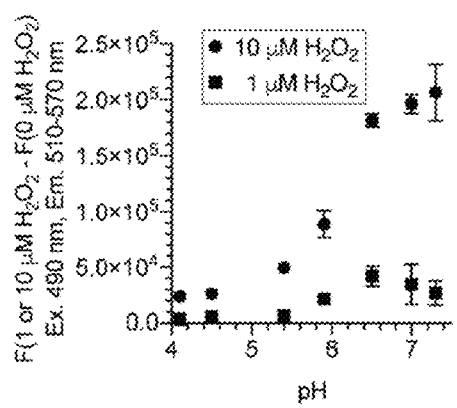
FIG. 14C

FLUOROGENIC PROBE USING A MISLOW-EVANS REARRANGEMENT FOR REAL-TIME IMAGING OF HYDROGEN PEROXIDE

CROSS-REFERENCE TO RELATED APPLICATIONS

This application claims the benefit of U.S. Provisional Patent Application No. 63/107,733, filed Oct. 30, 2020, the disclosure of which is hereby incorporated by reference in its entirety.

STATEMENT REGARDING FEDERALLY SPONSORED RESEARCH

This invention was made with government support under Grant Nos. 1506942 and 0911092 awarded by the National Science Foundation. The government has certain rights in the invention.

BACKGROUND OF THE INVENTION

Hydrogen peroxide ($H_2O_2$) is a reactive oxygen species (ROS) involved in many biological processes. As such, misregulation of $H_2O_2$ has been implicated in many diseases. In the cell, $H_2O_2$ is produced along with other ROS in the mitochondria and cytoplasm by the nicotinamide adenine dinucleotide phosphate (NADPH) oxidase family of enzymes, xanthine oxidase, and cytochrome P450 enzymes.

In light of the dichotomous nature of $H_2O_2$ in maintaining cellular homeostasis, it has become increasingly important to understand the detailed biology of $H_2O_2$. Only recently has the spatiotemporal presence of $H_2O_2$ in wound healing been recognized. Additionally, ROS production is critical for defense against pathogens; however, early studies used nonselective probes for ROS and could not distinguish between effects caused specifically by $H_2O_2$. Studies of biological $H_2O_2$ with high specificity and temporal resolution have relied on genetically-encoded protein-based probes. These studies using protein-based probes have revealed that upon injury to tissue, $H_2O_2$ is produced in seconds to minutes with gradients from the site of injury, facilitating the mobilization of immune cells. Those results have not been observed using chemical probes, likely due to the comparatively slow reaction kinetics. Most chemical probes for $H_2O_2$ have relied on the boronate ester functionality (FIG. 1A) for reaction, although other functionalities have been reported. Advances from these studies have allowed for selective detection of $H_2O_2$ over other reactive oxygen and nitrogen species (RNS). This chemistry presumably requires the presence of the hydroperoxide anion, $HOO^-$. Under biological conditions, the abundance of this species should be very low ($\approx 0.1\%$ of $H_2O_2$) because the pKa of $H_2O_2$ is 11.6. When these probes are applied in biological systems, it takes ~30 min to produce fluorescence signals.

Improved probes for rapid detection of $H_2O_2$ are needed.

SUMMARY

Provided herein is a compound having the structure:

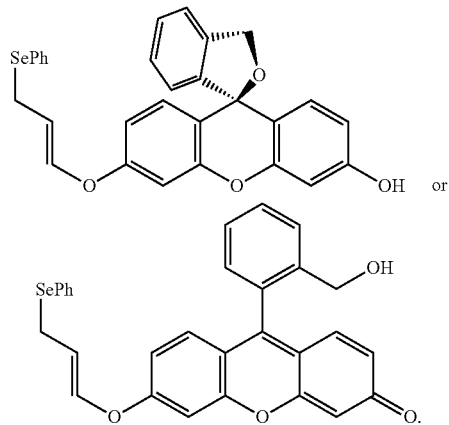

Provided herein is a compound having the structure:

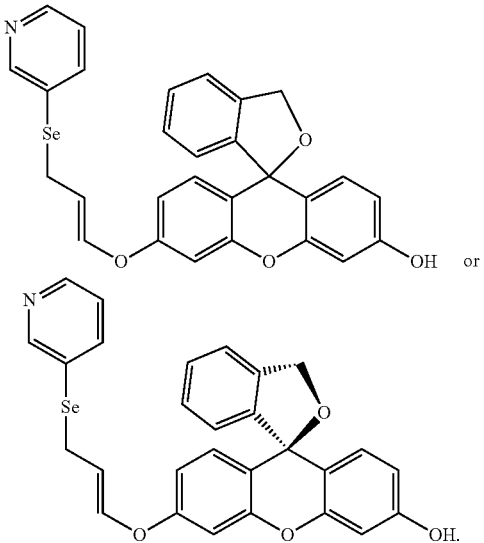

Provided herein is a compound having the structure:

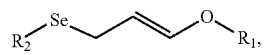

wherein:
- $R_1$ is a fluorescent dye moiety that does not fluoresce when incorporated in the compound or fluoresces with a different intensity or peak wavelength when incorporated in the compound; and
- $R_2$ is optionally substituted and is alkyl, e.g., $C_1$-$C_{10}$ alkyl; heteroalkyl, e.g., $C_1$-$C_{10}$ heteroalkyl; aryl; heteroaryl; or any combination of the preceding.

Also provided herein is a method of identifying or visualizing the presence of $H_2O_2$ in a cell, tissue, organ, or organism. The method comprises contacting the cell, tissue, organ, or organism with a compound according to any of the preceding paragraphs, illuminating the cell, tissue, organ, or organism with light including, or at an excitation wavelength for, the reaction product of the compound with $H_2O_2$, and detecting fluorescent emission from the reaction product.

Also provided herein is a method of identifying or quantifying the presence of $H_2O_2$ in a sample. The method comprises adding to or mixing in the sample a compound according to any of the preceding paragraphs, illuminating the sample with light including or at an excitation wavelength for the reaction product of the compound with $H_2O_2$, and detecting fluorescent emission from the reaction product.

The following numbered clauses provide various aspects or embodiments of the present invention.

Clause 1: A compound having the structure:

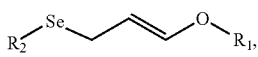

wherein: $R_1$ is a fluorescent dye moiety that does not fluoresce when incorporated in the compound or fluoresces with a different intensity or peak wavelength when incorporated in the compound; and $R_2$ is optionally substituted and is alkyl, e.g., $C_1$-$C_{10}$ alkyl; heteroalkyl, e.g., $C_1$-$C_{10}$ heteroalkyl; aryl; heteroaryl; or any combination of the preceding.

Clause 2: The compound of clause 1, wherein $R_1$ is a xanthene dye moiety, such as a fluorescein, rhodamine, or eosine dye moiety, or a substituted

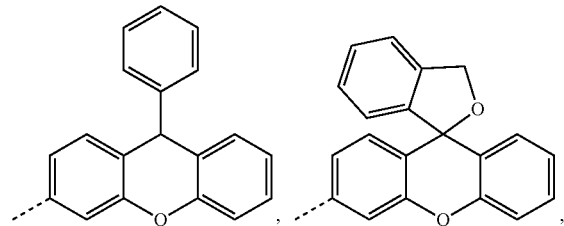

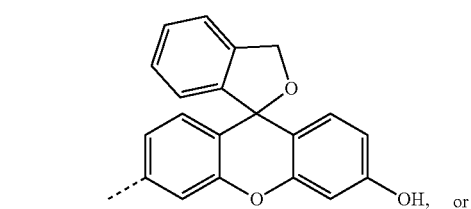

moiety, and $R_2$ is phenyl, optionally substituted aryl, optionally substituted heteroaryl, or $C_1$-$C_{10}$ alkyl.

Clause 3: The compound of clause 1 or 2, wherein $R_1$ is

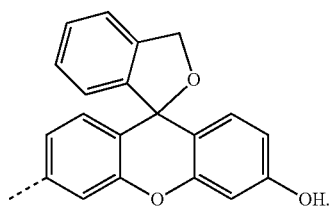

Clause 4: The compound of any one of clauses 1-3, wherein $R_1$ is

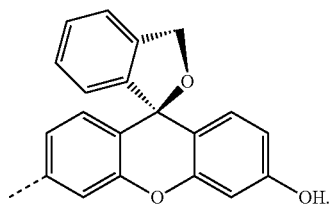

Clause 5: The compound of any one of clauses 1-4, wherein $R_2$ is phenyl.

Clause 6: The compound of any one of clauses 1-4, wherein $R_2$ is a nitrogen-substituted heteroaryl moiety, such as a pyridine moiety

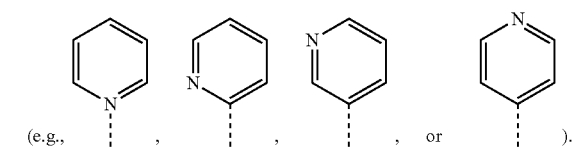

Clause 7: The compound of clause 6, wherein $R_2$ is a pyridine moiety.

Clause 8: The compound of clause 6 or 7, wherein $R_2$ is

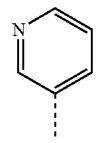

Clause 9: The compound of clause 1 having the structure:

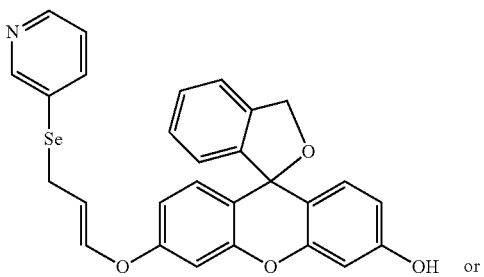

-continued

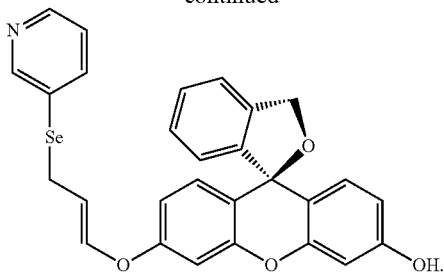

Clause 10: The compound of clause 1 having the structure:

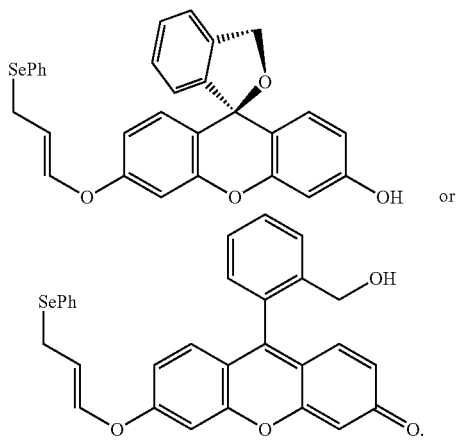

Clause 11: A method of identifying or visualizing the presence of $H_2O_2$ in a cell, tissue, organ, or organism, comprising contacting the cell, tissue, organ, or organism with a compound according to any one of clauses 1-10, illuminating the cell, tissue, organ, or organism with light including or at an excitation wavelength for the reaction product of the compound with $H_2O_2$, and detecting fluorescent emission from the reaction product.

Clause 12: The method of clause 11, further comprising obtaining an image of the cell, tissue, organ, or organism at or including light at the excitation wavelength for the reaction product of the compound with $H_2O_2$, optionally using fluorescence microscopy.

Clause 13: The method of clause 11, further comprising obtaining a spectrograph of light emitted by the reaction product, and optionally quantifying $H_2O_2$ based on light emitted by the reaction product.

Clause 14: The method of clause 11, further comprising sorting cells using a fluorescence-activated cell sorter, based on an amount of light emitted by the reaction product in each cell.

Clause 15: The method of clause 14, further comprising classifying cells sorted based on the amount of light emitted by the reaction product in each cell, and quantifying $H_2O_2$ production in the sorted cells based on the number of cells sorted.

Clause 16: A method of identifying or quantifying the presence of $H_2O_2$ in a sample, comprising adding to or mixing in the sample a compound according to any one of clauses 1-10, illuminating the sample with light including or at an excitation wavelength for the reaction product of the compound with $H_2O_2$, and detecting fluorescent emission from the reaction product.

Clause 17: The method of clause 16, wherein the sample is contained within a cuvette, multi-well plate, or lateral flow device, optionally wherein the cuvette, multi-well plate, or lateral flow device are disposable, or form part of a disposable article.

Clause 18: The method of clause 16 or 17, wherein the sample is a biological sample, such as blood, plasma, serum, urine, cerebrospinal fluid, mucus, lymph, cell lysate or a fraction or derivative thereof, or conditioned cell culture medium.

Clause 19: The method of any one of clauses 16-18, wherein the $H_2O_2$ is converted to a different compound in an enzyme-linked immunoassay, e.g., using catalase to decompose the $H_2O_2$ to water and oxygen, and the identification or quantification of the presence of the $H_2O_2$ measures the presence of or quantity of an analyte or binding activity detected by the immunoassay.

BRIEF DESCRIPTION OF THE DRAWINGS

The patent or application file contains at least one drawing executed in color. Copies of this patent or patent application publication with color drawing(s) will be provided by Office upon request and payment of the necessary fee.

FIGS. 14A-C. The fluorescence response of 1 (1 μM) at pH 7 (A) with increasing concentrations of $H_2O_2$ or (B) various ROS. A) 10 μM 1, 0-71.5 μM $H_2O_2$, 14.5:85.5 MeCN/50 mM phosphate pH 7, B) Data was normalized so that the reaction of 1 and $H_2O_2$ was set to 100. Excess ROS and RNS compared to 1 was used. C) The fluorescence response of 1 (10 μM) with $H_2O_2$ (0, 1, or 10 μM) at various pHs. 10 μM 1, 1:9 MeOH/25 mM phosphate in water, 20 min. The y-axis shows (fluorescence intensity with 1 or 10 μM $H_2O_2$)-(fluorescence intensity with no $H_2O_2$).

DETAILED DESCRIPTION

Figure 1A:
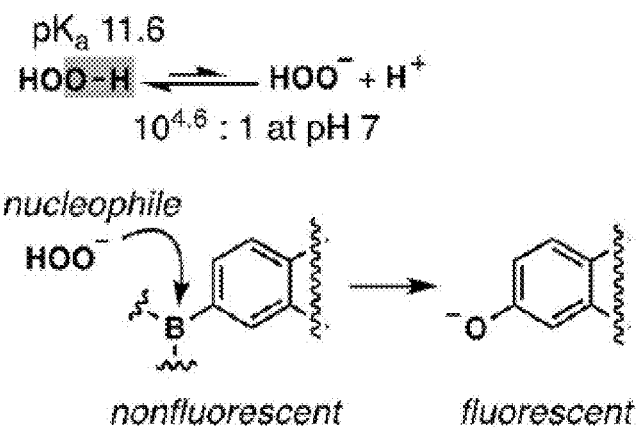
FIGS. 1A-B. Comparison of A) boronate-based and B) selenium-based probes for hydrogen peroxide.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include but are not limited to embodiments "consisting essentially of" and "consisting of" these stated elements or steps.

"Aryl," alone or in combination refers to an aromatic ring system such as phenyl or naphthyl. Multi-ring structures can be aromatic, such as anthracene, phenanthrene, or pyrene, as well as heterocyclic aromatic compounds, comprising one or more hetero-atoms, such as N, O, or S in place of a ring carbon, such as pyridine, pyrrole, furan, and thiophene. "Aryl" also can include aromatic ring systems that are optionally fused with a cycloalkyl ring. As an example, a xanthene dye is a triarylmethane dye in which two of the aromatic rings are also connected by an ether linkage to form a fused ring (xanthene) system. A "substituted aryl" is an aryl that is independently substituted with one or more substituents attached at any available atom to produce a stable compound, wherein the substituents are as described herein. The substituents can be, for example and without limitation, hydrocarbyl groups, alkyl groups, alkoxy groups, carboxyl-containing groups, ethers, and nitrate-containing groups. "Optionally substituted aryl" refers to aryl or substituted aryl. An aryloxy group can be, for example, an oxygen atom substituted with any aryl group, such as phenoxy. An arylalkoxy group can be, for example, an oxygen atom substituted with any aralkyl group, such as benzyloxy. "Arylene" denotes divalent aryl, and "substituted arylene" refers to divalent substituted aryl. "Optionally substituted arylene" refers to arylene or substituted arylene. A "polycyclic aryl group" and related terms, such as "polycyclic aromatic group" refers to a group composed of at least two fused aromatic rings. "Heteroaryl" or "hetero-substituted aryl" refers to an aryl group substituted with one or more heteroatoms, such as N, O, P, and/or S.

As used herein, "alkyl" refers to straight, branched chain, or cyclic hydrocarbon groups including, for example, from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of straight alkyl groups include methyl, ethyl, propyl, butyl, pentyl, hexyl, heptyl, octyl, nonyl, and decyl. Branched alkyl groups comprises any straight alkyl group substituted with any number of alkyl groups. Non-limiting examples of branched alkyl groups include isopropyl, isobutyl, sec-butyl, and t-butyl. Non-limiting examples of cyclic alkyl groups include cyclopropyl, cyclobutyl, cyclopentyl, cyclohexyl, cycloheptlyl, and cyclooctyl groups. Cyclic alkyl groups also comprise fused-, bridged-, and spiro-bicycles and higher fused-, bridged-, and spiro-systems. A cyclic alkyl group can be substituted with any number of straight, branched, or cyclic alkyl groups. "Substituted alkyl" can include alkyl substituted at 1 or more (e.g., 1, 2, 3, 4, 5, or even 6) positions, which substituents are attached at any available atom to produce a stable compound, with substitution as described herein. "Optionally substituted alkyl" refers to alkyl or substituted alkyl. "Alkylene" and "substituted alkylene" can include divalent alkyl and divalent substituted alkyl, respectively, including, without limitation, methylene, ethylene, trimethylene, tetramethylene, pentamethylene, hexamethylene, hepamethylene, octamethylene, nona methylene, or decamethylene. "Optionally substituted alkylene" can include alkylene or substituted alkylene.

"Alkene or alkenyl" can include straight, branched chain, or cyclic hydrocarbyl groups including, e.g., from 2 to about 20 carbon atoms, such as, without limitation $C_{2-3}$, $C_{2-6}$, $C_{2-10}$ groups having one or more, e.g., 1, 2, 3, 4, or 5, carbon-to-carbon double bonds. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. "Substituted alkene" can include alkene substituted at 1 or more, e.g., 1, 2, 3, 4, or 5 positions, which substituents are attached at any available atom to produce a stable compound, with substitution as described herein. "Optionally substituted alkene" can include alkene or substituted alkene. Likewise, "alkenylene" can refer to divalent alkene. Examples of alkenylene include without limitation, ethenylene (—CH=CH—) and all stereoisomeric and conformational isomeric forms thereof. "Substituted alkenylene" can refer to divalent substituted alkene. "Optionally substituted alkenylene" can refer to alkenylene or substituted alkenylene.

The term "alkoxy" can refer to an —O-alkyl group having the indicated number of carbon atoms. An ether or an ether group comprises an alkoxy group. For example, a ($C_1$-$C_6$) alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_1$-$C_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof. The term "ether" or "oxygen ether" refers to an alkyl group wherein one or more of the alkyl group's carbon atoms is replaced with an —O— group. Exemplary ethers include polyethylene glycol, diethylether, methylhexyl ether and the like.

"Carboxyl" or "carboxylic" refers to group having an indicated number of carbon atoms, where indicated, and terminating in a —C(O)OH group, thus having the structure —R—C(O)OH, where R is an unsubstituted or substituted divalent organic group that can include linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc. "Amine" or "amino" refers to group having the indicated number of carbon atoms, where indicated, and terminating in a —NH$_2$ group, thus, having the structure —R—NH$_2$, where R is a unsubstituted or substituted divalent organic group that, e.g. includes linear, branched, or cyclic hydrocarbons, and optionally comprises one or more heteroatoms. The term "alkylamino" refers to a radical of the formula —NHR$^x$ or —NR$^x$R$^x$ where each R$^x$ is, independently, an alkyl radical as defined above.

"Carbonyl" refers to the —C(O)— moiety within a substituent, such as a alkyl substituent on an aromatic ring, thereby forming a ketone or aldehyde substituent.

"Heteroatom" refers to any atom other than carbon or hydrogen, for example, N, O, P, and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with any atom other than carbon or hydrogen, for example, N, O, P, or S.

Terms combining the foregoing refer to any suitable combination of the foregoing, such as arylalkenyl, arylalkynyl, heteroarylalkyl, heteroarylalkenyl, heterocyclylalkyl, heterocyclylalkenyl, aryl, heteroaryl, heterocyclyl, cycloalkyl, cycloalkenyl, alkylarylalkyl, alkylarylalkenyl, alkenylarylalkyl, alkenylarylalkenyl, alkylheteroarylalkyl, alkylheteroarylalkenyl, alkenylheteroarylalkyl, alkenylheteroarylalkenyl, alkylheterocyclylalkyl, alkylheterocyclylalkenyl, alkenylheterocyclylalkyl, alkenylheterocyclylalkenyl, alkylaryl, alkenylaryl, alkylheteroaryl, or alkenylheteroaryl. As an example, "arylalkylene" refers to a divalent alkylene wherein one or more hydrogen atoms in an alkylene group is replaced by an aryl group, such as a ($C_3$-$C_8$)aryl group. Examples of ($C_3$-$C_8$)aryl-($C_1$-$C_6$)alkylene groups include without limitation 1-phenylbutylene, phenyl-2-butylene, 1-phenyl-2-methylpropylene, phenylmethylene, phenylpropylene, and naphthylethylene. The term "($C_3$-$C_8$)cycloalkyl-($C_1$-$C_6$)alkylene" refers to a divalent alkylene wherein one or more hydrogen atoms in the $C_1$-$C_6$ alkylene group is replaced by a ($C_3$-$C_8$)cycloalkyl group. Examples of ($C_3$-$C_8$)cycloalkyl-($C_1$-$C_6$)alkylene groups include without limitation 1-cycloproylbutylene, cyclopropyl-2-butylene, cyclopentyl-1-phenyl-2-methylpropylene, cyclobutylmethylene, and cyclohexylpropylene.

By "substituted" it is meant that one or more hydrogen atoms of a moiety or group, such as an aryl group is substituted with one or more other groups, referred to herein as "substituents". Non-limiting examples of substituents that may be included in xanthene dyes include one or more of: carbonyl, carboxyl or carboxylic acid, hydroxyl, thiol, $C_1$-$C_6$ alkyl hydroxyl, $C_1$-$C_6$ alkyl ester, $C_1$-$C_6$ alkyl, $C_1$-$C_6$ alkoxyl, $C_1$-$C_6$ alkyl ether, halo (e.g., F, Br, I), —O$^-$, amine, quaternary amine, $C_1$-$C_6$ alkyl-substituted amine, $C_1$-$C_6$ alkoxy-substituted amine, $C_1$-$C_6$ ether-substituted amine, phenyl, $C_1$-$C_6$ alkyl phenyl, sulfonyl, sulfone, or halophenyl.

Xanthene dyes, including derivatives thereof, such as rhodamine and its derivatives, such as, for example and without limitation, rhodamine 6G, rhodamine 123, and rhodamine B among many others, which are available commercially and which can be readily modified to include the allylic selenite moiety as described herein by conventional methods. Example of xanthene dye moieties include, without limitation: substituted moieties, such as, for example and without limitation,

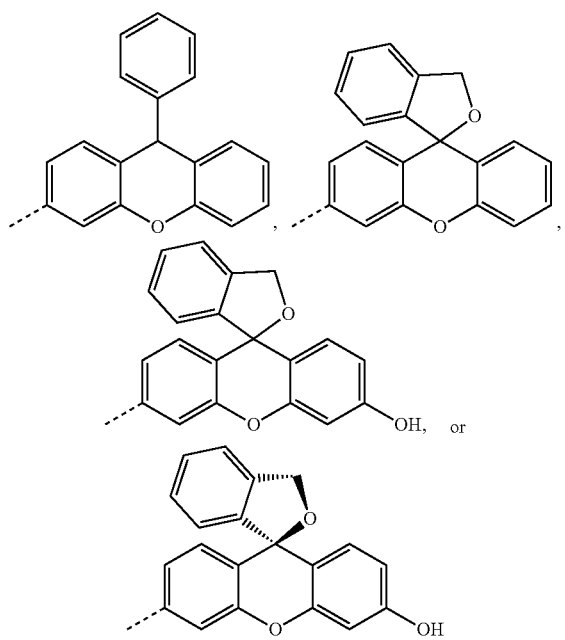

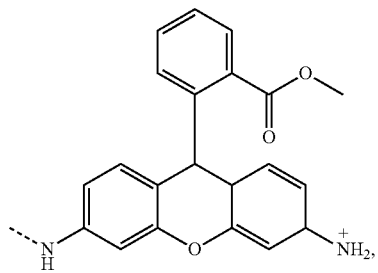

based on the rhodamine derivative, rhodamine 123. The dotted line referring to the bond connecting the illustrated moiety to the remainder of the compound, representing a saturated or unsaturated bond.

The compound may be:

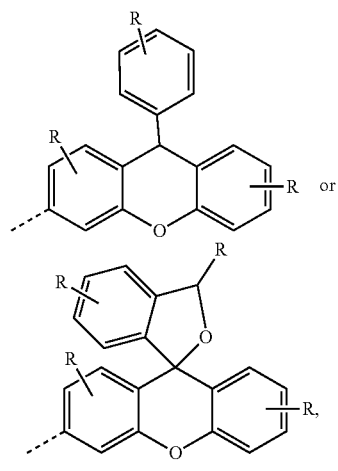

where one or more instances of R is present on each ring, and may be H (unsubstituted) or one or more instance of R is, independently, a substituent, examples of which include, without limitation: carbonyl, carboxyl or carboxylic acid, hydroxyl, thiol, $C_1$-$C_6$ alkyl hydroxyl, $C_1$-$C_6$ alkyl ester, $C_1$-$C_6$ alkyl, $C_1$-$C_6$ alkoxyl, $C_1$-$C_6$ alkyl ether, halo (e.g., F, Br, I), —O⁻, amine, quaternary amine, $C_1$-$C_6$ alkyl-substituted amine, $C_1$-$C_6$ alkoxy-substituted amine, $C_1$-$C_6$ ether-substituted amine, phenyl, $C_1$-$C_6$ alkyl phenyl, sulfonyl, sulfone, or halophenyl. R also may be one or more additional, linked xanthene dye moieties. R may be cyclic, aryl, or fused cyclic ring structures/moieties, that are optionally substituted. As would be appreciated to those of ordinary skill in the art, the variety of additional substituents in known and commercially-available xanthene dyes, such as rhodamines, is significant, and as such the listed substituents are merely exemplary.

The compounds provided herein have the general structure:

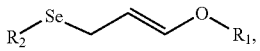

wherein $R_1$ is a fluorescent dye moiety that does not fluoresce when incorporated in the compound or fluoresces with a different intensity or peak wavelength when incorporated in the compound. Stated another way, the fluorophore or an aryl moiety of the fluorophore, is substituted with

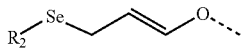

and the fluorophore fluoresces differently when

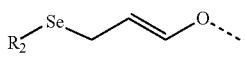

is converted to ⁻O••• in the presence of $H_2O_2$, for example, according to the described Seleno-Mislow-Evans rearrangement and acetal hydrolysis mechanism. $R_2$ is optionally substituted and is alkyl, e.g., $C_1$-$C_{10}$ alkyl; heteroalkyl, e.g., $C_1$-$C_{10}$ heteroalkyl; aryl; heteroaryl; phenyl; or any combination of the preceding.

$R_1$ may be a xanthene dye moiety. The xanthene dye moiety may include xanthene dyes, including derivatives thereof, such as rhodamine and its derivatives, such as, for example and without limitation, rhodamine 6G, rhodamine 123, and rhodamine B among many others, which are available commercially and which can be readily modified to include the allylic selenite moiety as described herein by conventional methods. Examples of xanthene dye moieties include, without limitation: substituted

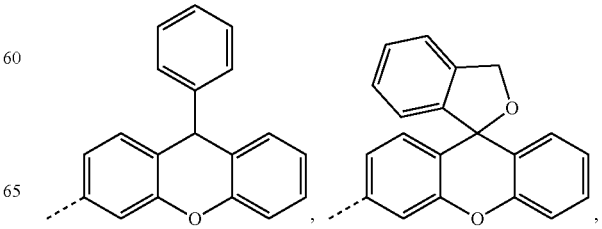

-continued

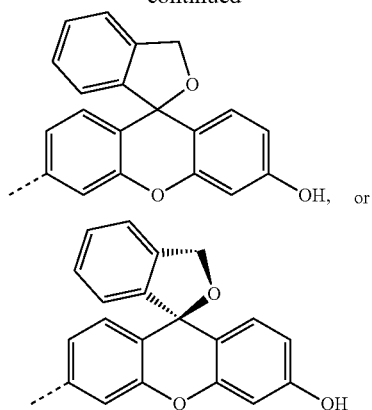

moieties, such as, for example and without limitation,

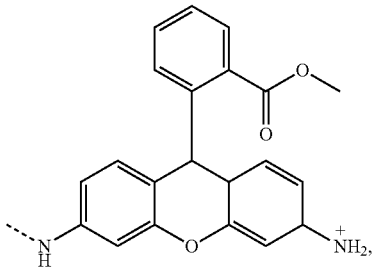

based on the rhodamine derivative, rhodamine 123. The xanthene dye moiety may also be a fluorescein or eosine dye moiety. The dotted line referring to the bond connecting the illustrated moiety to the remainder of the compound, representing a saturated or unsaturated bond.

$R_2$ may be optionally substituted and may be alkyl; heteroalkyl; aryl; heteroaryl; or any combination of the preceding. $R_2$ may be alkyl such as $C_1$-$C_{10}$ alkyl. $R_2$ may be heteroalkyl such as $C_1$-$C_{10}$ heteroalkyl. $R_2$ may be phenyl, optionally substituted aryl, optionally substituted heteroaryl, or $C_1$-$C_{10}$ alkyl. $R_2$ may be phenyl. $R_2$ may be a nitrogen-substituted heteroaryl moiety. The nitrogen-substituted heteroaryl moiety may be a pyridine moiety. The pyridine moiety may be

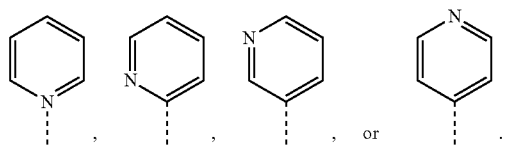

$R_2$ may be a pyridine moiety, such as

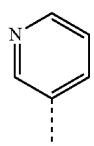

The compound may have the structure:

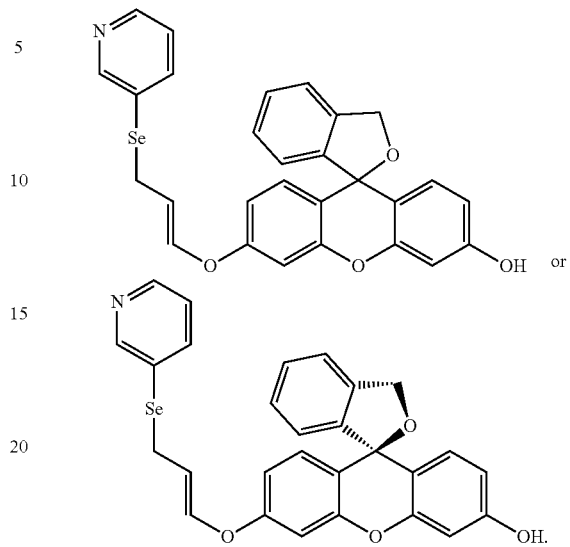

A method of identifying or visualizing the presence of $H_2O_2$ in a cell, tissue, organ, or organism is also provided. The method includes contacting the cell, tissue, organ, or organism with the compound described herein. The cells, tissue, organ, or organism may be on a microscope slide. The method includes illuminating the cell, tissue, organ, or organism with light or at an excitation wavelength for the reaction product of the compound with $H_2O_2$. The method includes detecting fluorescent emission from the reaction product. Fluorescence microscopy, and related methods, and any suitable imaging system, e.g., as are commercially-available, such as, without limitation, confocal microscopy systems, may be used to visualize a cell, tissue, an organ, or an organism and/or detect the fluorescent output of the reaction product exposed to light at or containing an excitation wavelength for the reaction product.

The method may include obtaining an image of the cell, tissue, organ, or organism at or including light at the excitation wavelength for the reaction product of the compound with $H_2O_2$. Obtaining an image of the cell, tissue, organ, or organism at or including light at the excitation wavelength for the reaction product of the compound with $H_2O_2$ may be done using fluorescence microscopy. The method may include obtaining a spectrograph of light emitted by the reaction product. The method may include quantifying $H_2O_2$ based on light emitted by the reaction product. The method may include sorting cells using a fluorescence-activated cell sorter, based on an amount of light emitted by the reaction product in each cell. The method may include classifying cells sorted based on the amount of light emitted by the reaction product in each cell, and quantifying $H_2O_2$ production in the sorted cells based on the number of cells sorted.

A method of identifying or quantifying the presence of $H_2O_2$ in a sample is also provided. The method includes adding to or mixing in the sample the compound described herein. The method includes illuminating the sample with light including or at an excitation wavelength for the reaction product of the compound with $H_2O_2$. The method includes detecting fluorescent emission from the reaction product.

The sample may be contained within a cuvette, multi-well plate, or lateral flow device. The cuvette, multi-well plate, or lateral flow device may be disposable, or may form part of a disposable article. The sample may be a biological sample. The biological sample may be blood, plasma, serum, urine, cerebrospinal fluid, mucus, lymph, cell lysate or a fraction or derivative thereof, or conditioned cell culture medium.

All compounds described herein, unless specifically indicated otherwise include any and all stereoisomers or stereoisomer mixtures thereof, free bases, or salts thereof.

Examples

Figure 1B:
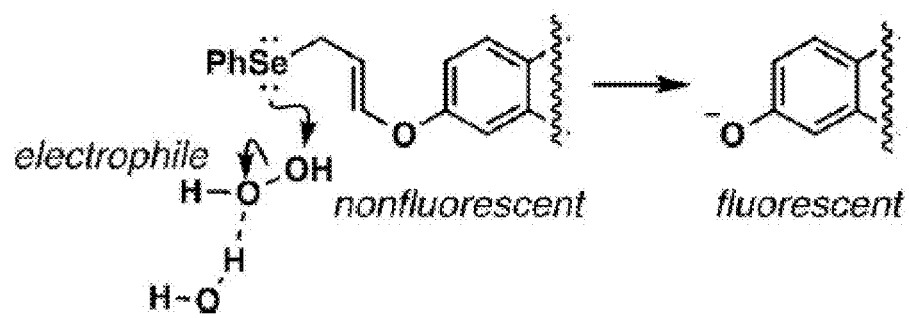

To develop a new probe that more rapidly reacts intracellularly, the seleno Mislow-Evans rearrangement was used, which undergoes the oxidation of an allylic selenide with $H_2O_2$ (FIG. 1B). (P. Bickart, F. W. Carson, J. Jacobus, E. G. Miller, K. Mislow, *J. Am. Chem. Soc.* 1968, 90, 4869-4876; and D. A. Evans, G. C. Andrews, Acc. Chem. Res. 1974, 7, 147-155; c) H. J. Reich, *J. Org. Chem.* 1975, 40, 2570-2572). This rearrangement is fast even at 0° C. and requires the neutral and abundant form of $H_2O_2$ to act as an electrophile; this reactivity has not been exploited in the development of probes for $H_2O_2$. It was hypothesized that the seleno Mislow-Evans rearrangement would provide a novel platform for the fluorometric detection of $H_2O_2$ with superior kinetics to more favorably compete with the degradation of $H_2O_2$ in cells. Here, the rearrangement is integrated with a spontaneous hydrolysis of the resulting acetal to translate the high reactivity of a selenium atom with $H_2O_2$ into a fluorogenic switch. The present disclosure presents the synthesis of selenide 1 and its selectivity for $H_2O_2$ over other ROS and RNS. It is also shown that selenide 1 can detect endogenously produced $H_2O_2$ by treatment with ionomycin in macrophages and in a zebrafish wound-healing experiment.

All reactions were carried out with freshly distilled solvents under anhydrous conditions, unless otherwise noted. All of the flasks used for carrying out reactions were dried in an oven at 80° C. prior to use. Unless specifically stated, the temperature of a water bath during the evaporation of organic solvents using a rotary evaporator was about 35±5° C. All of the syringes in this study were dried in an oven at 80° C. and stored in a desiccator over Drierite®. Tetrahydrofuran (THF) was distilled over sodium metal and benzophenone. Methylene chloride ($CH_2Cl_2$) was distilled over calcium hydride. Acetonitrile was distilled from $CaH_2$ and stored over 3 Å molecular sieves. Yields refer to chromatographically and spectroscopically ($^1H$ NMR) homogenous materials, unless otherwise stated. All reactions were monitored by thin-layer chromatography (TLC) carried out on 0.25-mm Merck silica gel plates (60F-254) using UV light (254 nm) for visualization or a solution of anisaldehyde in ethanol or a solution of 2.4% phosphomolybdic acid, 1.4% phosphoric acid, and 5% sulfuric acid in water as a developing agents and heat for visualization. Silica gel (230-400 mesh) was used for flash column chromatography. A rotary evaporator was connected to a water aspirator that produced a vacuum pressure of approximately 60 mmHg when it was connected to the evaporator. NMR spectra were recorded on a Bruker Advance spectrometer at 300 MHz or 400 MHz. The chemical shifts are given in parts per million (ppm) on a delta (δ) scale. The solvent peak was used as a reference value: for $^1H$ NMR: $CHCl_3$=7.27 ppm, $CH_3OH$=3.31 ppm, $CH_3CN$=2.08 ppm; for $^{13}C$ NMR: $CDCl_3$=77.00 ppm, $CD_3OD$=49.00 ppm, and $CD_3CN$=1.79 ppm for $CD_3$ or 118.26 ppm for CN. The following abbreviations are used to indicate the multiplicities: s=singlet; d=doublet; t=triplet; q=quartet; m=multiplet; br=broad. High-resolution mass spectra (HRMS) were recorded on a VG 7070 spectrometer. Infrared (IR) spectra were collected on a Mattson *Cygnus* 100 spectrometer. Samples for acquiring IR spectra were prepared as a thin film on a NaCl plate by dissolving the compound in $CH_2Cl_2$ and then evaporating the $CH_2Cl_2$.

All fluorescence measurements (excitation 490 nm, emission 510-570 nm) were carried out using a Promega Biosystems Modulus II Microplate Reader or a HoribaMax Fluorometer unless otherwise stated. Data analysis was performed using GraphPad Prism 8.

It is envisioned that allylic selenide 1 (FIG. 2A) could undergo oxidation with $H_2O_2$ through transition state TS1, followed by the Mislow-Evans rearrangement of selenoxide 2 and the subsequent hydrolysis of selenenate 3 to form the brightly fluorescent phenol 5. For the conversion of 3 to 5, two pathways are plausible. The first pathway is the nucleophilic cleavage of the Se—O bond of 3 to form hemiacetal 4, which spontaneously forms phenoxide 5 and acrolein (Pathway 1). The second is the oxidation of selenenate 3 to seleninate 6 en route to phenol 5 via hemiacetal 4 (Pathway 2). As shown below, the actual pathway is experimentally determined.

The synthesis of selenide 1 (FIG. 2B) commenced with the conjugate addition of fluorescein methyl ester 7 to methyl propiolate to afford ester 8 in 79% yield.

Synthesis of methyl (E)-2-(6-((3-methoxy-3-oxoprop-1-en-1-yl)oxy)-3-oxo-3H-xanthen-9-yl)benzoate (8)

The following procedure was used for the synthesis of methyl (E)-2-(6-((3-methoxy-3-oxoprop-1-en-1-yl)oxy)-3-oxo-3H-xanthen-9-yl)benzoate 8, i.e.,

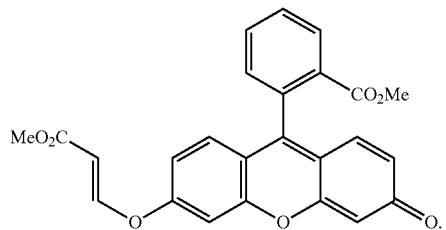

A suspension of fluorescein methyl ester 7 (7.760 g, 22.52 mmol) in dry $CH_2Cl_2$ (390 mL) was treated with N-methylmorpholine (683 mg, 6.76 mmol) and methyl propiolate (9.467 mg, 112.6 mmol) under a nitrogen atmosphere at 23° C. After stirring the reaction mixture for 24 h at the same temperature, silica gel (24 g) was added, and the mixture was concentrated in vacuo. The resulting crude residue was purified by flash column chromatography (10☐90% EtOAc in hexanes) on silica gel (560 mL) to obtain vinyl ether 8 (7.65 g, 79%) as an orange solid.

Figure 3A:
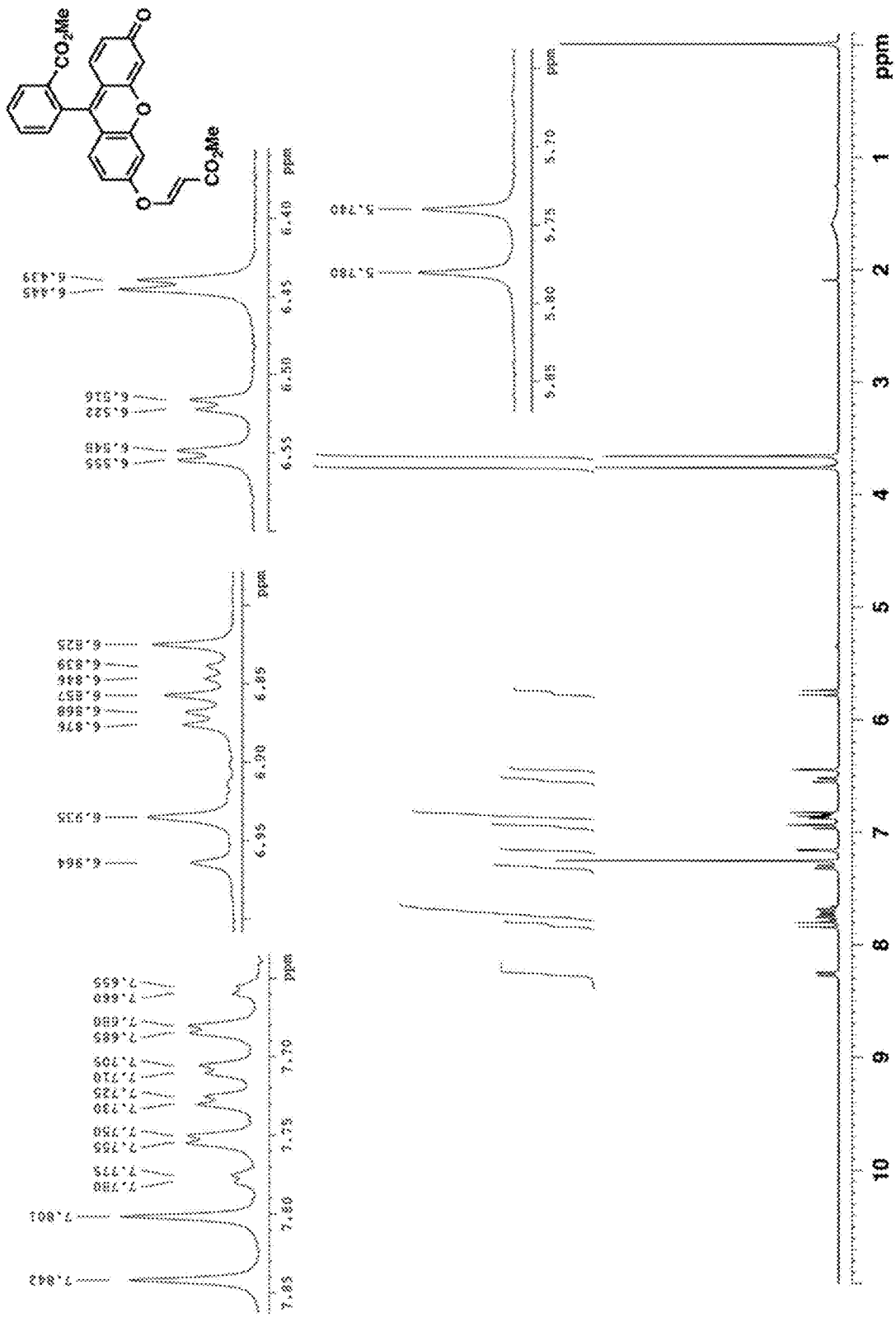
FIGS. 3A-B. A) $^1H$ NMR spectrum and B) $^{13}C$ NMR spectrum for methyl (E)-2-(6-((3-methoxy-3-oxoprop-1-en-1-yl)oxy)-3-oxo-3H-xanthen-9-yl)benzoate.
Figure 3B:
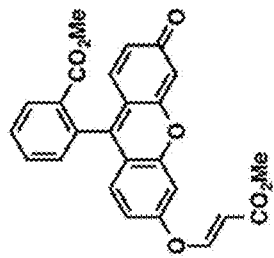
Figure 3B:
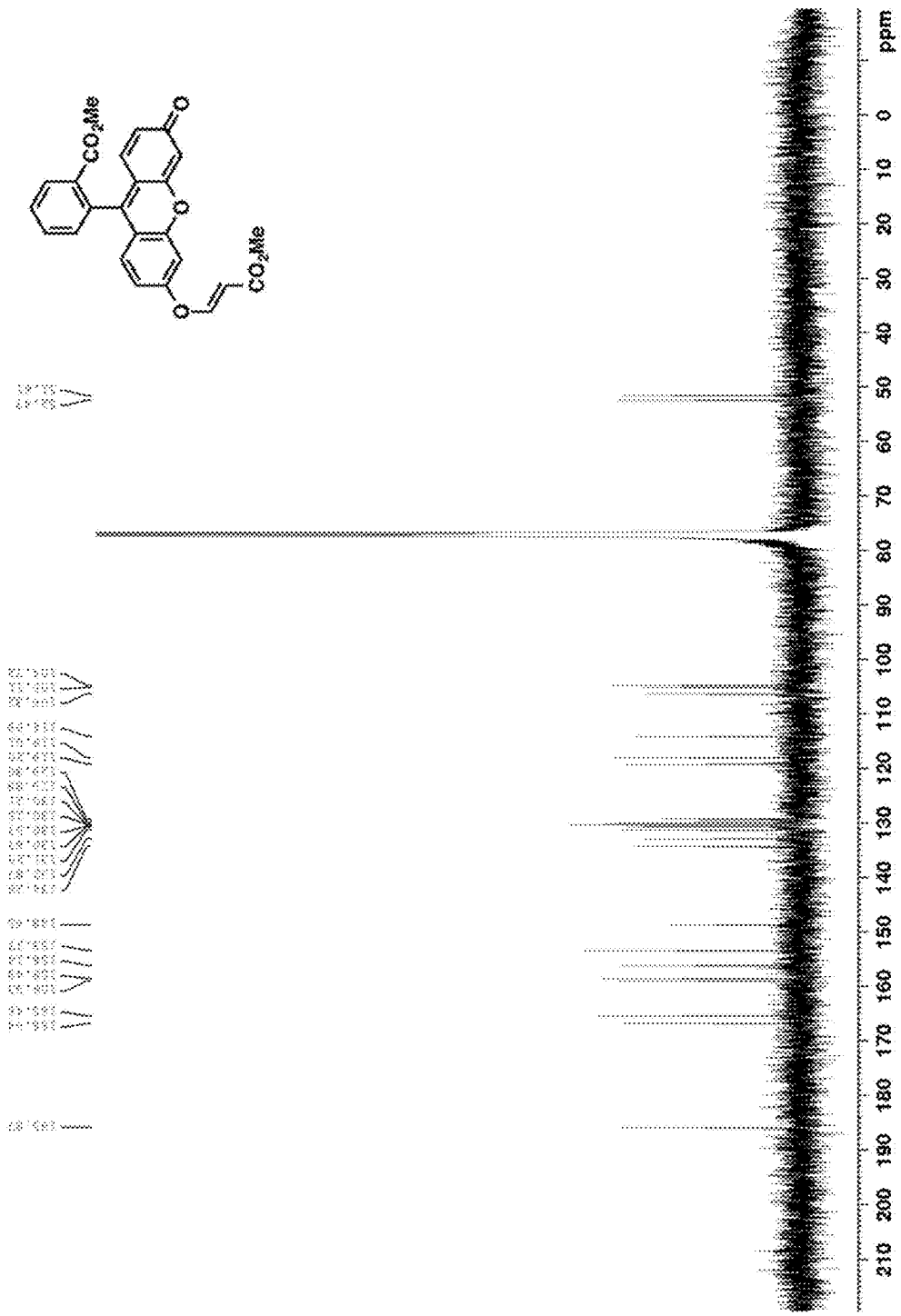

Data for 8: melting point: 192.0-193.0° C.; $R_f$: 0.25 (70% EtOAc in hexanes); IR (film): ☐$_{max}$=3060, 2923, 1722 (C═O), 1642 (C═O), 1639 (C═O), 1595, 1522, 1444, 1378, 1267, 1247, 1191, 1158, 1133, 1106, 1081, 854, 707 cm 1; $^1H$ NMR (300 MHz, $CDCl_3$, 293 K): δ 8.25 (dd, J=7.5, 1.5 Hz, 1H), 7.85 (d, J=12.0 Hz, 1H), 7.79 (ddd, J=7.5, 7.5, 1.2 Hz, 1H), 7.72 (ddd, J=7.5, 7.5, 1.2 Hz, 1H), 7.33 (dd, J=7.5, 1.2 Hz, 1H), 7.18 (d, J=2.4 Hz, 1H), 6.98 (d, J=9.0 Hz, 1H), 6.89 (dd, J=9.6, 1.8 Hz, 1H), 6.87 (d, J=9.6 Hz, 1H), 6.56 (dd, J=9.6, 1.8 Hz, 1H), 6.46 (d, J=1.8 Hz, 1H), 5.79 (d, J=12.0 Hz, 1H), 3.76 (s, 3H), 3.66 (s, 3H) (FIG. 3A); $^{13}C$ NMR (100 MHz, $CDCl_3$, 293 K): δ 185.9, 166.8, 165.5, 158.9, 158.5, 156.1, 153.4, 148.7, 134.3, 132.9, 131.3, 130.7, 130.6, 130.3, 130.2, 129.9, 129.3, 119.2, 118.0, 114.1, 106.3, 105.1, 104.7, 52.5, 51.6 (FIG. 3B); HRMS (ESI-TOF) m/z: [M+H]+ calculated for $C_{25}H_{19}O_7$ 431.1110, found 431.1125.

The following DIBALH reduction formed alcohol 9 in 66% yield.

Synthesis of (S,E)-6'-((3-Hydroxyprop-1-en-1-yl)oxy)-3H-spiro[isobenzofuran-1,9'-xanthen]-3'-ol (9)

The following procedure was used for the synthesis of (S,E)-6'-((3-Hydroxyprop-1-en-1-yl)oxy)-3H-spiro[isobenzofuran-1,9'-xanthen]-3'-ol 9, i.e.,

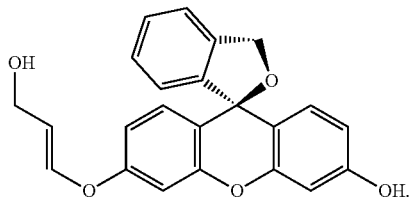

A 1 M solution of diisobutylaluminum hydride in hexanes (1.80 mL, 1.80 mmol) was added dropwise to a flask containing ester 8 (100 mg, 0.23 mmol) in dry $CH_2Cl_2$ (1.5 mL) under a nitrogen atmosphere at −78° C. After stirring the reaction mixture for 15 min at the same temperature, the flask was warmed to 23° C. The mixture was stirred at the same temperature for an additional 2 h, and then the reaction was quenched with 1 M aqueous sodium potassium tartrate (2 mL) at 0° C. After stirring the mixture for 3 h at 23° C., $Et_2O$ (5 mL) and DDQ (57 mg, 0.25 mmol) were added at 0° C. and the resulting mixture was stirred at the same temperature for 1 h. The combined organic and aqueous layers were filtered through a pad of Celite, and the pad was rinsed with EtOAc. The filtrate was dried under $Na_2SO_4$, filtered through a cotton plug, and concentrated in vacuo. The resulting crude residue was purified by flash column chromatography (10→60% EtOAc in hexanes) on silica gel (20 mL) to obtain alcohol 9 (57 mg, 66%) as a pale yellow solid and byproduct 5 (14 mg, 20%) as an orange solid.

Figure 4A:
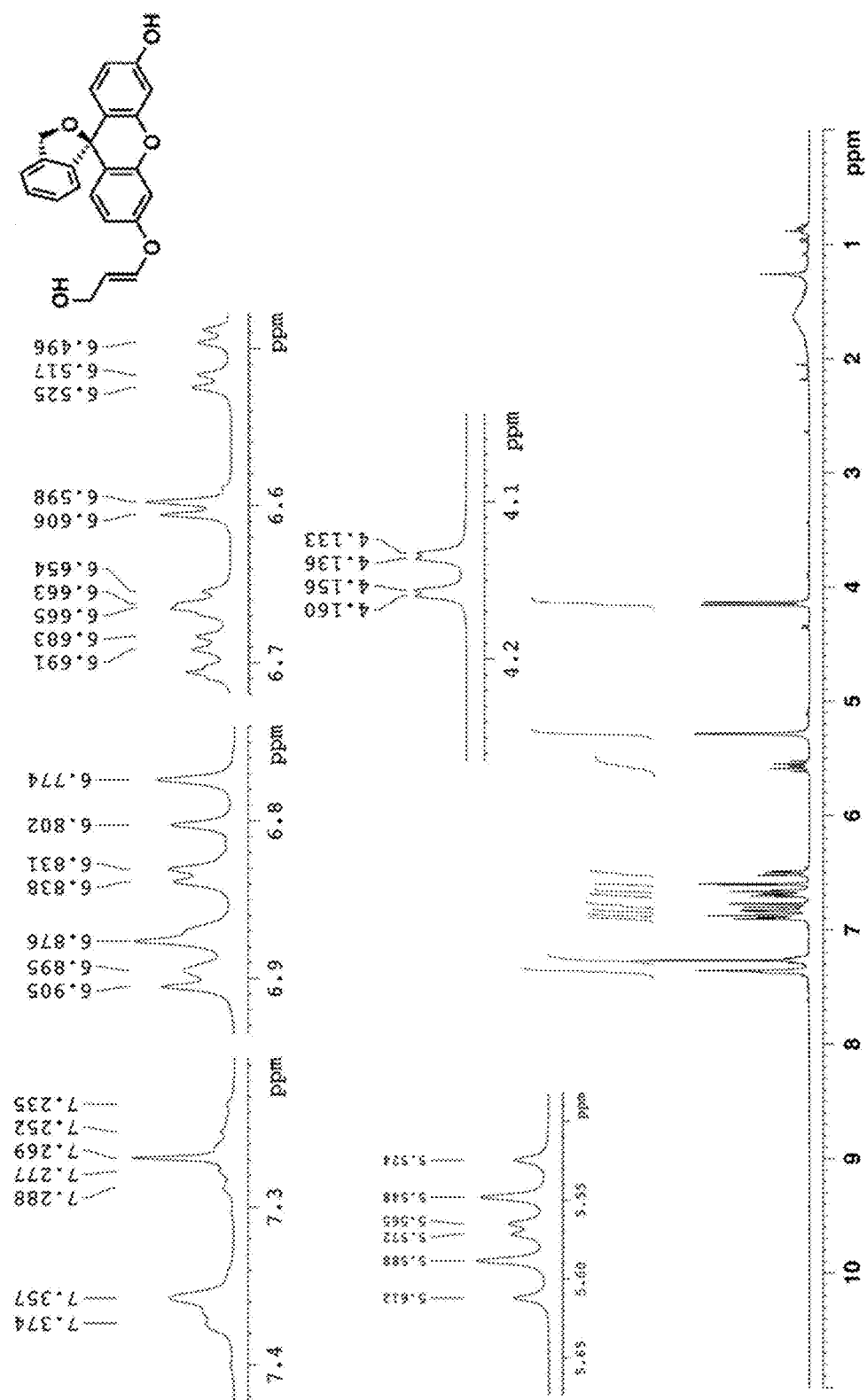
FIGS. 4A-B. A) $^1H$ NMR spectrum and B) $^{13}C$ NMR spectrum for (S,E)-6'-((3-Hydroxyprop-1-en-1-yl)oxy)-3H-spiro[isobenzofuran-1,9'-xanthen]-3'-ol.
Figure 4B:
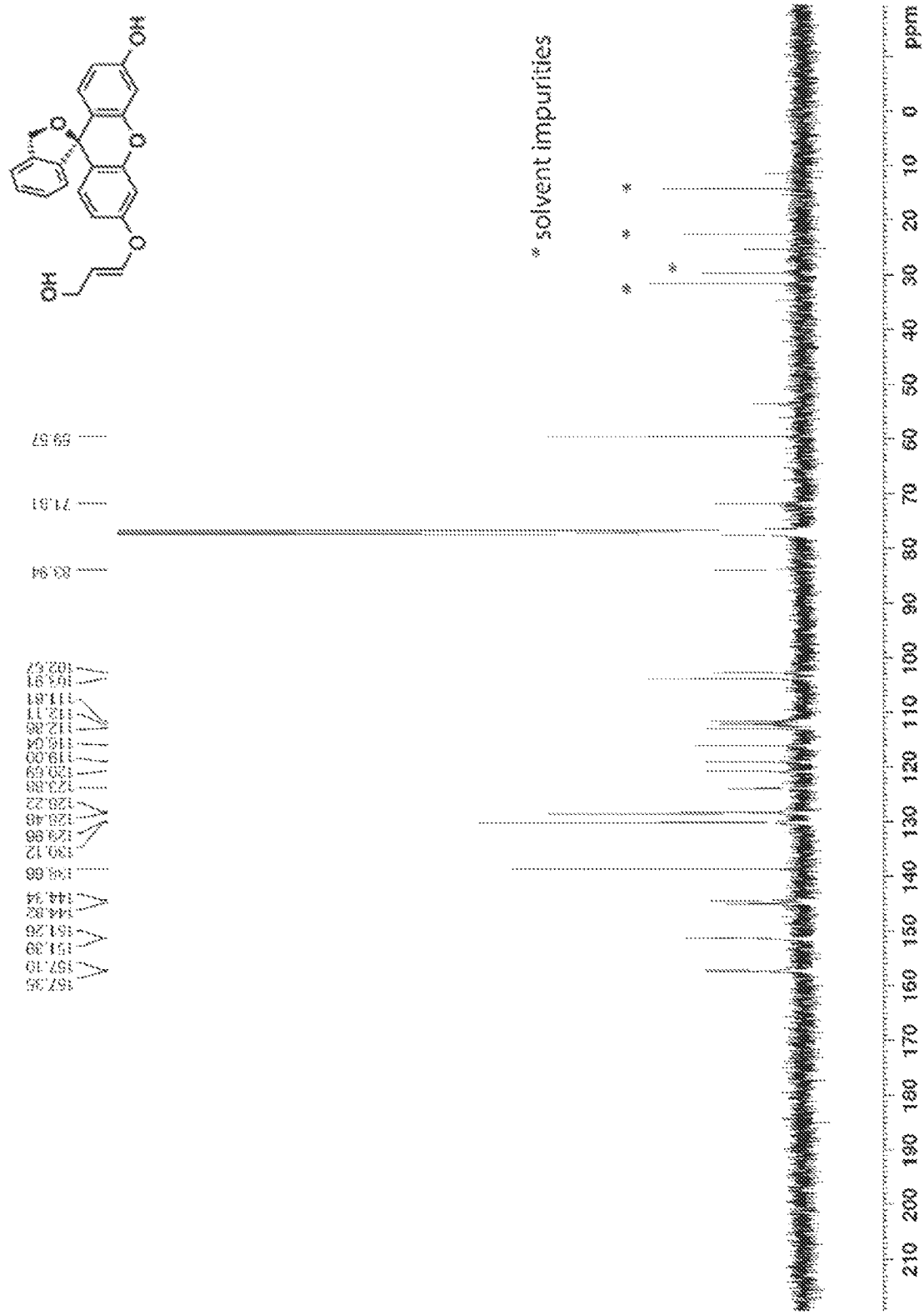

Data for 9: melting point: 169.0-170.0° C.; $R_f$: 0.52 (70% EtOAc in hexanes); IR (film): $\square_{max}$=3378 (O—H), 2923, 2853, 1673, 1601, 1480, 1434, 1409, 1266, 1173, 1114, 1004, 926, 854, 722 cm-1; $^1$H NMR (300 MHz, 1% $CD_3OD$ in $CDCl_3$, 293 K): δ 7.36-7.37 (m, 2H), 7.23-7.28 (m, 1H), 6.91 (d, J=2.4 Hz, 1H), 6.88 (br s, 1H), 6.84 (d, J=2.4 Hz, 1H), 6.77 (d, J=8.4 Hz, 1H), 6.68-6.70 (m, 1H), 6.70 (dt, J=12.0, 1.8 Hz, 1H), 6.60 (d, J=2.4 Hz, 1H), 6.52 (dd, J=8.7, 2.4 Hz, 1H), 5.57 (dt, J=12.0, 7.2 Hz, 1H), 5.29 (s, 2H), 4.15 (dd, J=7.2, 1.8 Hz, 2H) (FIG. 4A); $^{13}$C NMR (100 MHz, $CDCl_3$, 293 K): δ 157.4, 157.1, 151.4, 151.3, 144.8, 144.3, 138.7, 130.1, 130.0, 128.5, 128.2, 123.9, 120.7, 119.0, 116.0, 112.9, 112.1, 111.6, 103.9, 102.7, 83.9, 71.8, 59.6 (FIG. 4B); HRMS (ESI-TOF) m/z: [M+H]+ calculated for $C_{23}H_{19}O_5$ 375.1227, found 375.1209.

The moderate yield was caused by the hydrolysis of the enol ether during aqueous workup. The final Mitsunobu-type reaction afforded selenide 1 in 41% yield. The structure was confirmed by the X-ray structure analysis.

Synthesis of (S,E)-6'-((3-(Phenylselanyl)prop-1-en-1-yl)oxy)-3H-spiro[isobenzofuran-1,9'-xanthen]-3'-ol (1)

The following procedure was used for the synthesis of (S,E)-6'-((3-(Phenylselanyl)prop-1-en-1-yl)oxy)-3H-spiro[isobenzofuran-1,9'-xanthen]-3'-ol 1, i.e.,

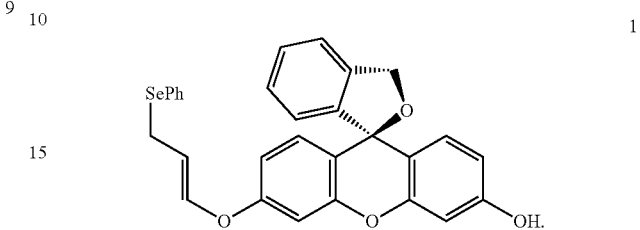

A 10-mL round-bottomed flask equipped with a Teflon-coated magnetic stir bar containing alcohol 9 (85 mg, 0.23 mmol) was purged with argon. The flask was treated with THF (1.2 mL), $^nBu_3P$ (67 μL, 0.27 mmol), and PhSeCN (29 μL, 0.23 mmol) sequentially at 0° C. The mixture was stirred at the same temperature for 30 min and was then quenched with saturated $NH_4Cl$. The quenched mixture was extracted with EtOAc (3×15 mL). The combined organic layers were dried over $Na_2SO_4$ and concentrated in vacuo. The resulting crude residue was purified by flash column chromatography ($SiO_2$, eluent: 5%→25% EtOAc in hexanes; 30 mL each) to obtain 1 (48 mg, 41%) as pale-yellow solid.

Figure 5A:
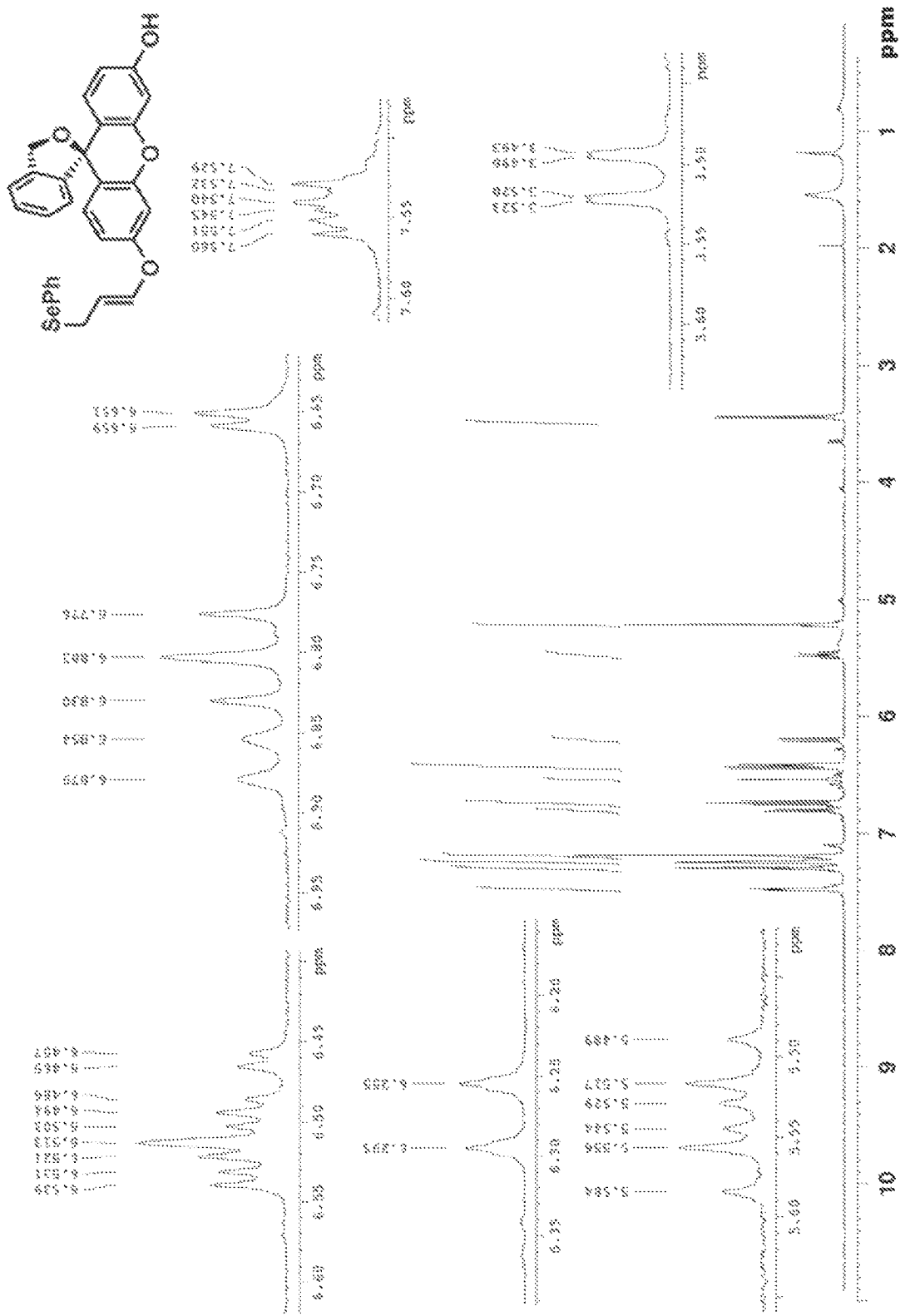
FIGS. 5A-B. A) $^1H$ NMR spectrum and B) $^{13}C$ NMR spectrum for S,E)-6'-((3-(Phenylselanyl)prop-1-en-1-yl)oxy)-3H-spiro[isobenzofuran-1,9'-xanthen]-3'-ol.
Figure 5B:
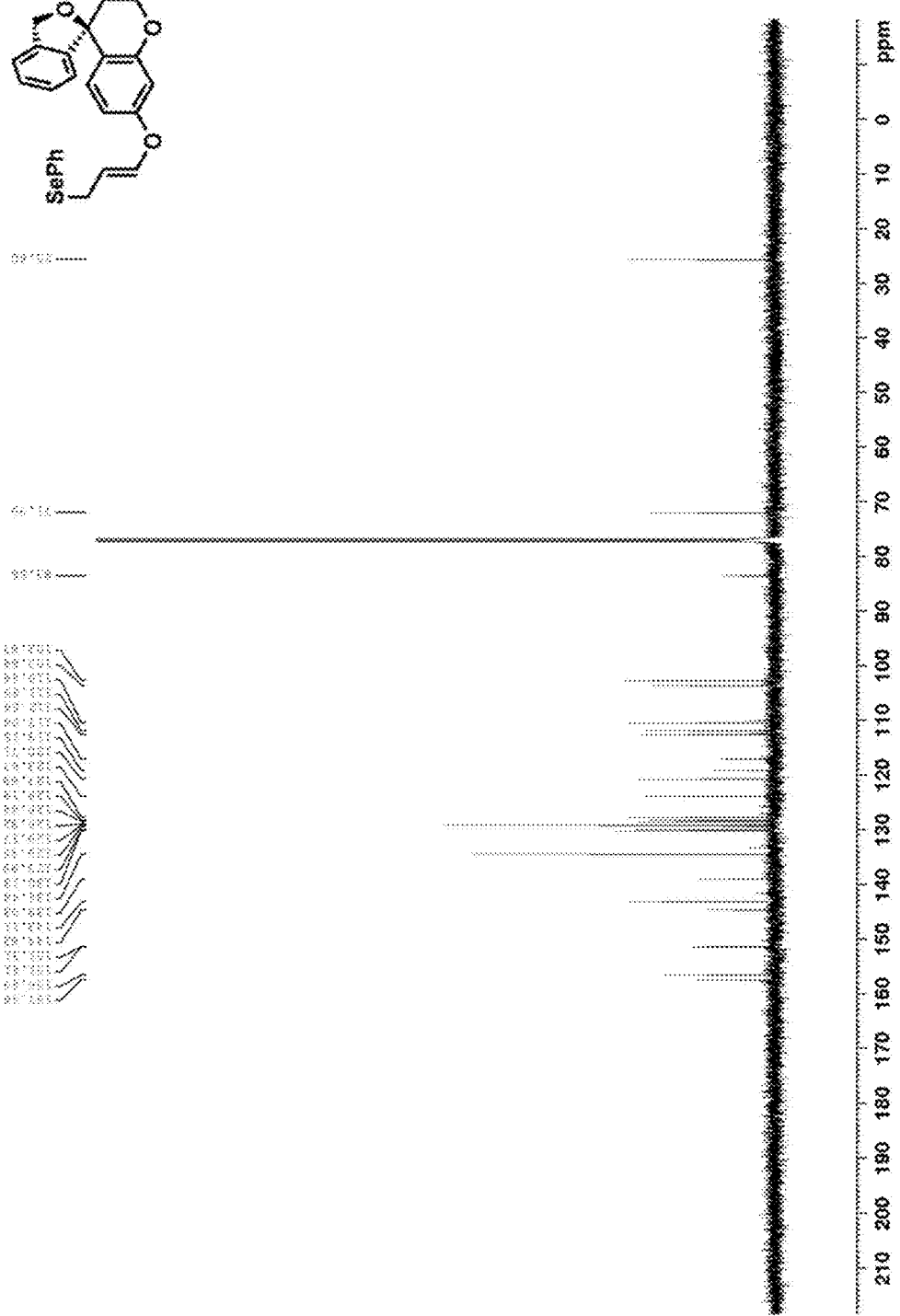

Data for 1: melting point: 125.5-126.5° C.; $R_f$: 0.56 (40% EtOAc in hexanes); IR (film): $\square_{max}$=3286 (broad, O—H), 2923, 2853, 2360, 1664, 1609, 1496, 1458, 1427, 1331, 1266, 1247, 1210, 1177, 1111, 997, 928, 846, 804, 757, 737, 691 cm$^{-1}$; $^1$H NMR (300 MHz, 1% $CD_3OD$ in $CDCl_3$, 293 K): δ 7.56 (dd, J=6.0, 1.2 Hz, 2H), 7.36-7.34 (m, 2H), 7.32-7.31 (m, 3H), 7.27-7.26 (m, 1H), 6.88 (d, J=7.5 Hz, 1H), 6.83 (dd, J=8.1, 8.1 Hz, 2H), 6.66 (d, J=2.4 Hz, 1H), 6.54 (m, 3H), 6.30 (d, J=12.0 Hz, 1H), 5.57 (dt, J=12.0, 8.4 Hz, 1H), 5.27 (s, 2H), 3.45 (dd, J=8.1, 0.9 Hz, 2H) (FIG. 5A); $^{13}$C NMR (100 MHz, $CDCl_3$, 293 K): δ 157.5, 156.5, 151.4, 151.3, 144.6, 143.1, 139.0, 134.4, 133.2, 130.1, 130.0, 129.4, 129.2, 128.9, 128.5, 128.2, 127.7, 123.9, 120.7, 119.1, 117.0, 112.5, 111.9, 110.5, 103.6, 102.7, 83.6, 72.0, 25.6 (FIG. 5B); HRMS (ESI-TOF) m/z: [M−H]+ calculated for $C_{29}H_{21}O_4Se$ 513.0610, found 513.0610.

Figure 2A:
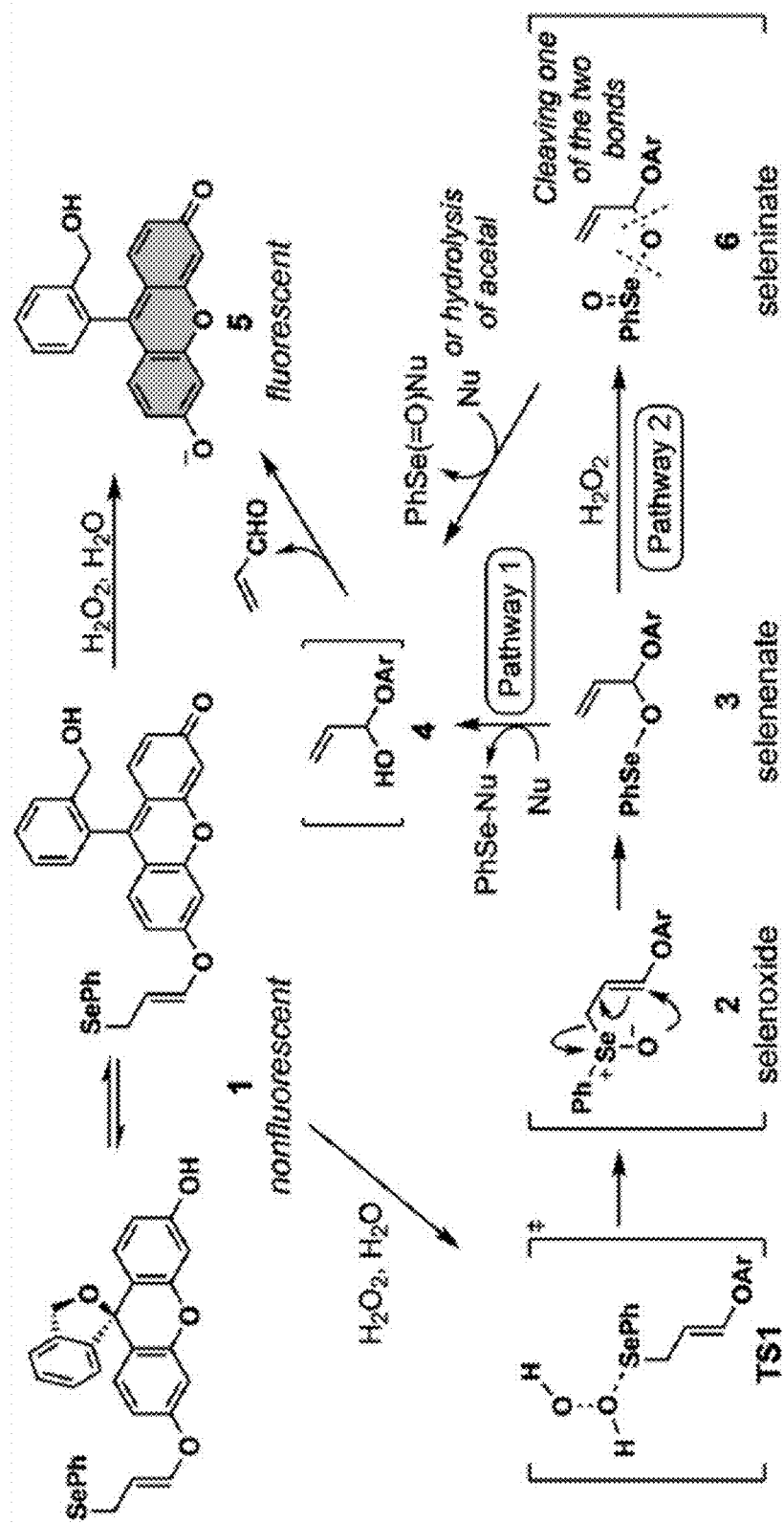
FIGS. 2A-B. A) Design of probe 1 based on the seleno-Mislow-Evans rearrangement followed by hydrolysis via two possible pathways. B) Synthesis of probe 1. Conditions: A) N-Methylmorpholine (0.3 equiv), methyl propiolate (5.0 equiv), $CH_2Cl_2$, 24 h, 79%; B) DIBALH (7.8 equiv), $CH_2Cl_2$, −78 to 23° C., 2 h; then DDQ (1.1 equiv), $Et_2O$, 3 h, 0° C., 66%; c) $^nBu_3P$ (1.2 equiv), PhSeCN (1.0 equiv), THF, 0° C., 30 min, 41%.
Figure 2B:
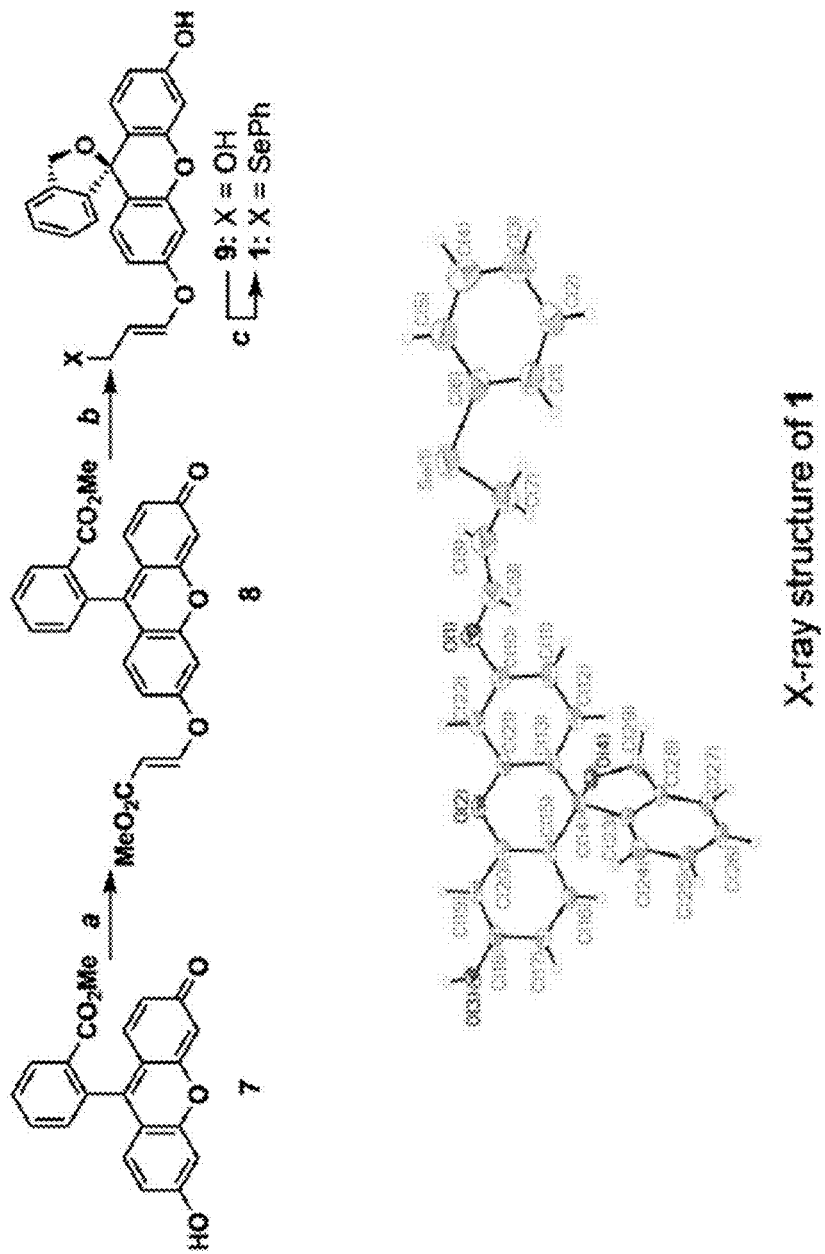

To investigate the mechanism of the reaction between selenide 1 and $H_2O_2$ as depicted in FIG. 2A, the reaction was monitored in situ by $^1$H NMR spectroscopy. Probe 1 (1.8 mg) in $CD_3OD$ (0.75 mL) was treated with 943 mM $H_2O_2$ (1.9 μL). The crude reaction mixture was monitored in situ by $^1$H NMR spectroscopy and analyzed against known standards (phenol 5 and acrolein). FIGS. 3A-F shows that both 5 and acrolein were formed during the reaction.

Figure 6:
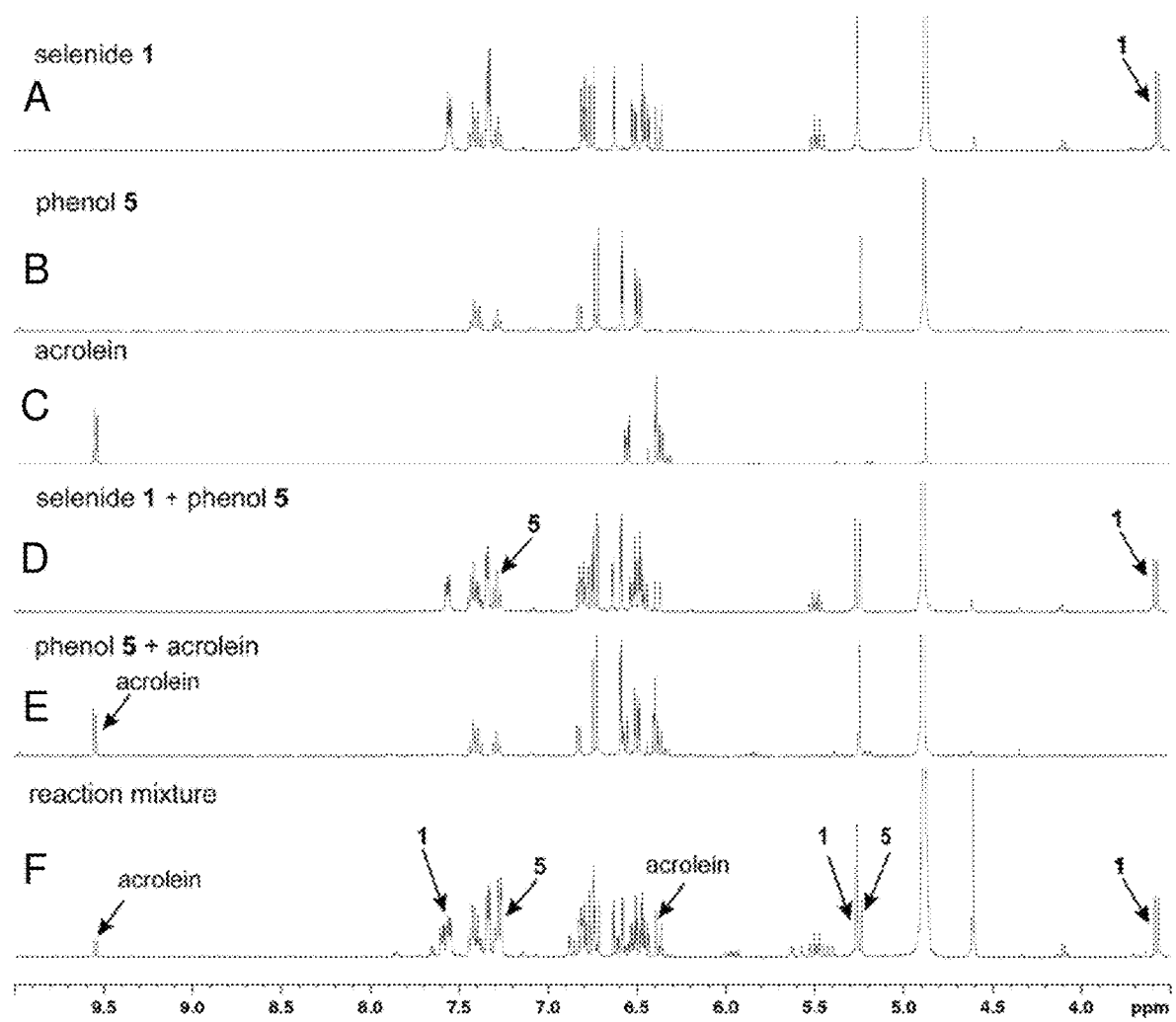
FIG. 6. Mechanistic studies $^1H$ NMR (400 MHz, $CD_3OD$) spectra of A) selenide 1, B) phenol 5, C) acrolein, D) selenide 1 and phenol 5 (1:1), E) acrolein and phenol 5 (1:1), F) reaction mixture of selenide 1 and $H_2O_2$.
Figure 7A:
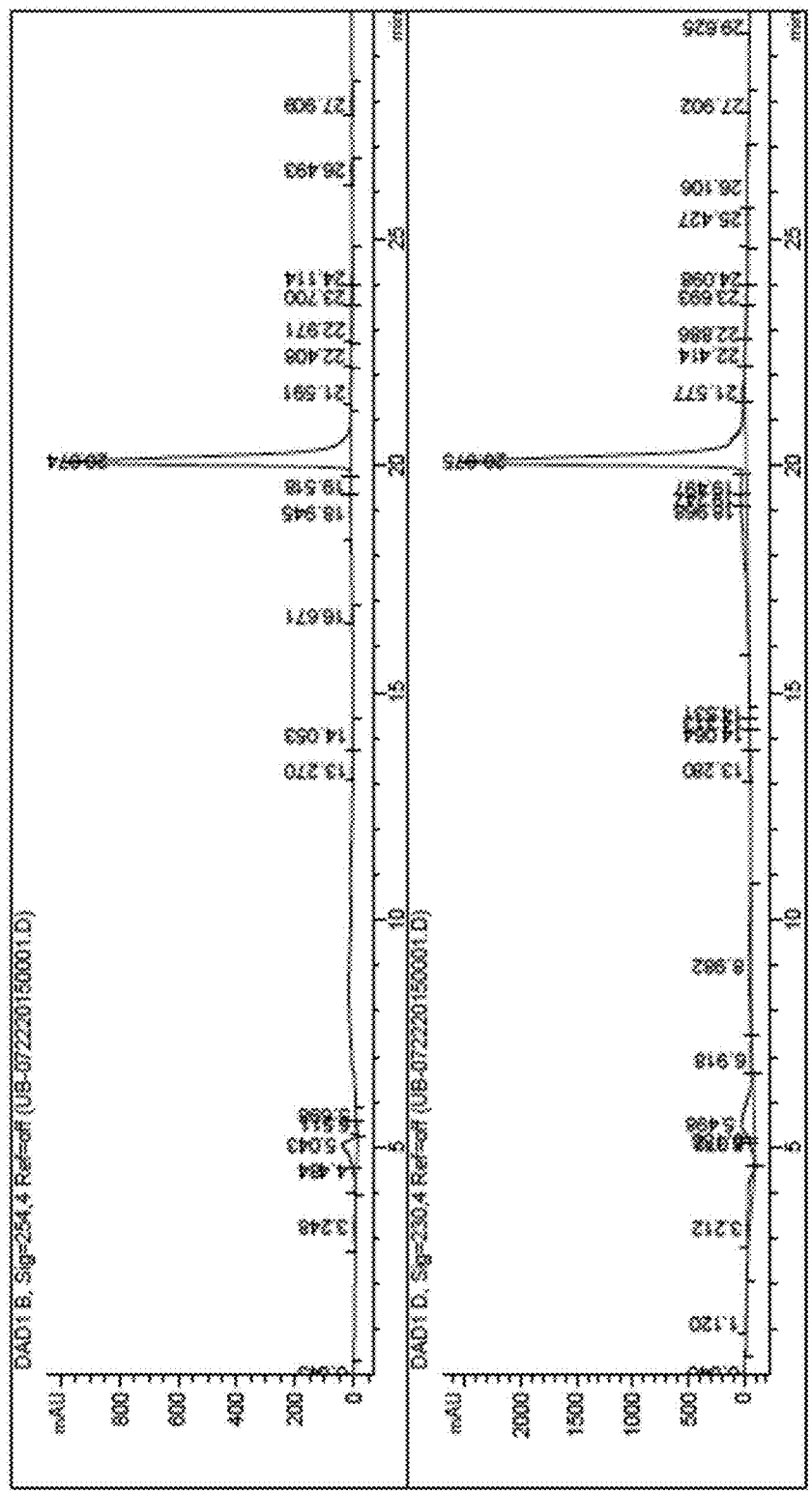
FIGS. 7A-E. HPLC chromatograms of A) authentic sample of selenide 1, B) phenol 5, C) selenide 1+phenol 5, D) crude reaction mixture of selenide 1+1 equiv. $H_2O_2$, and E) authentic sample of $PhSeO_2H$ acquired at λ=254 nm and 230 nm, respectively.
Figure 7B:
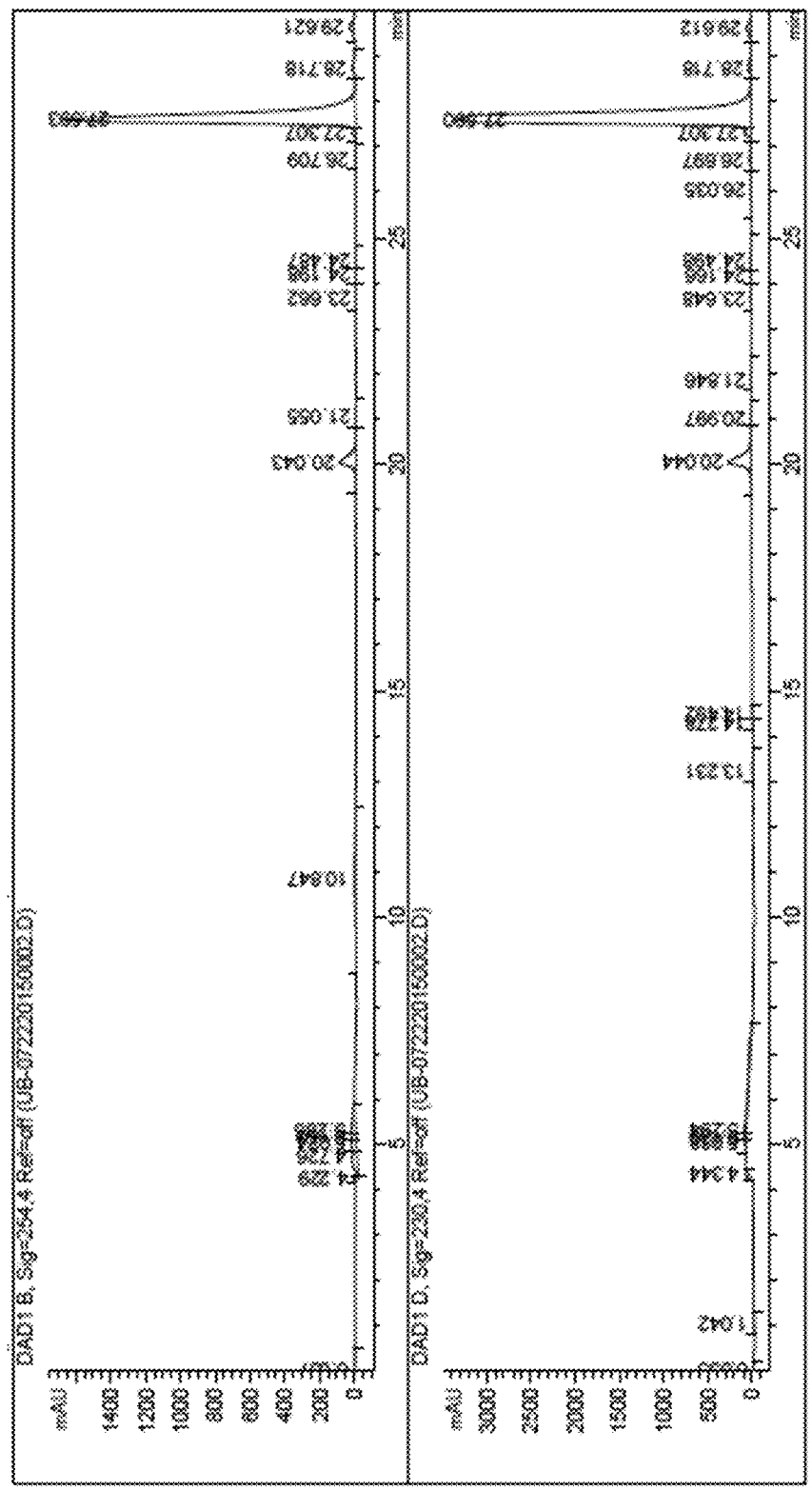
Figure 7C:
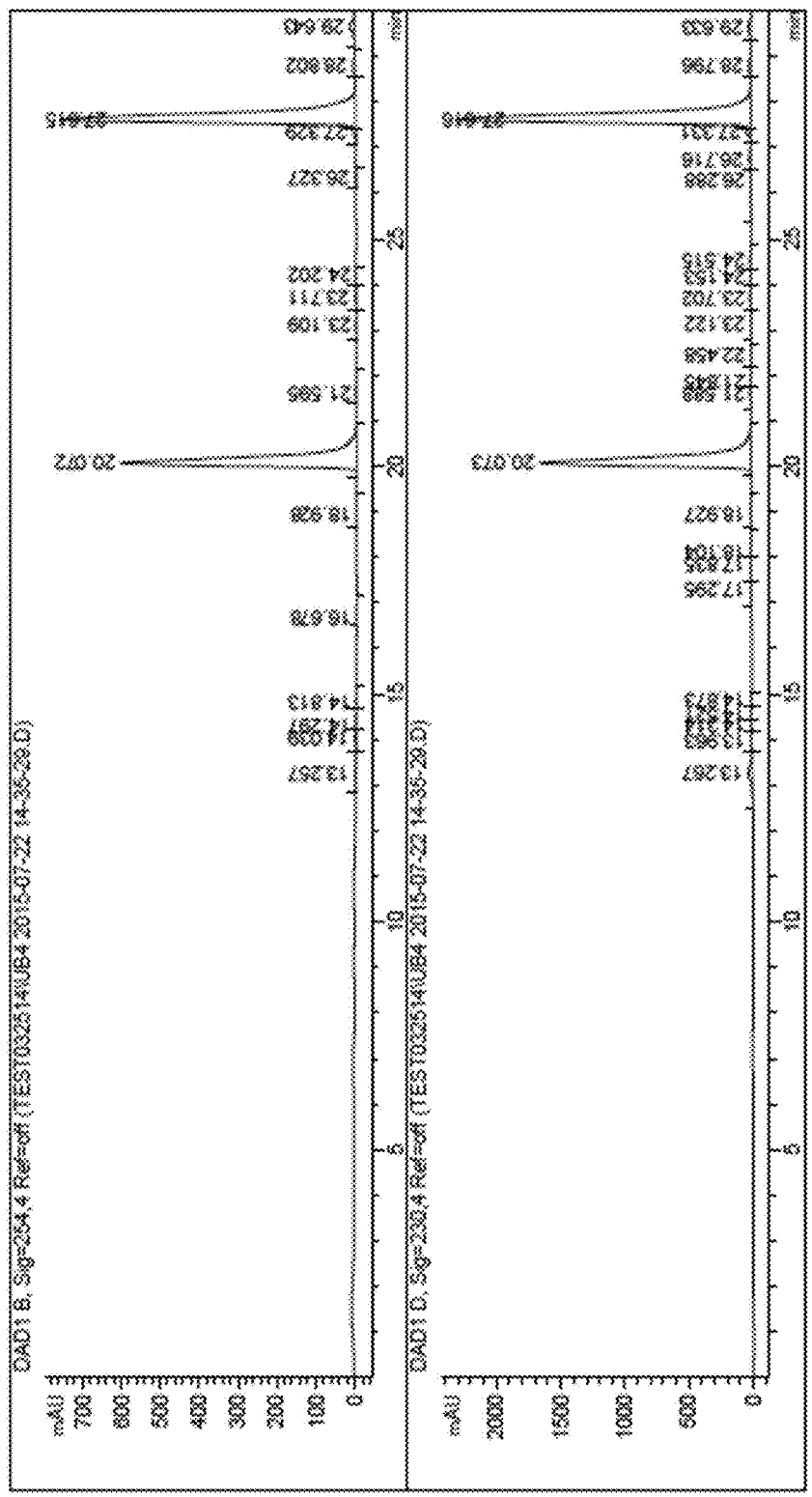
Figure 7D:
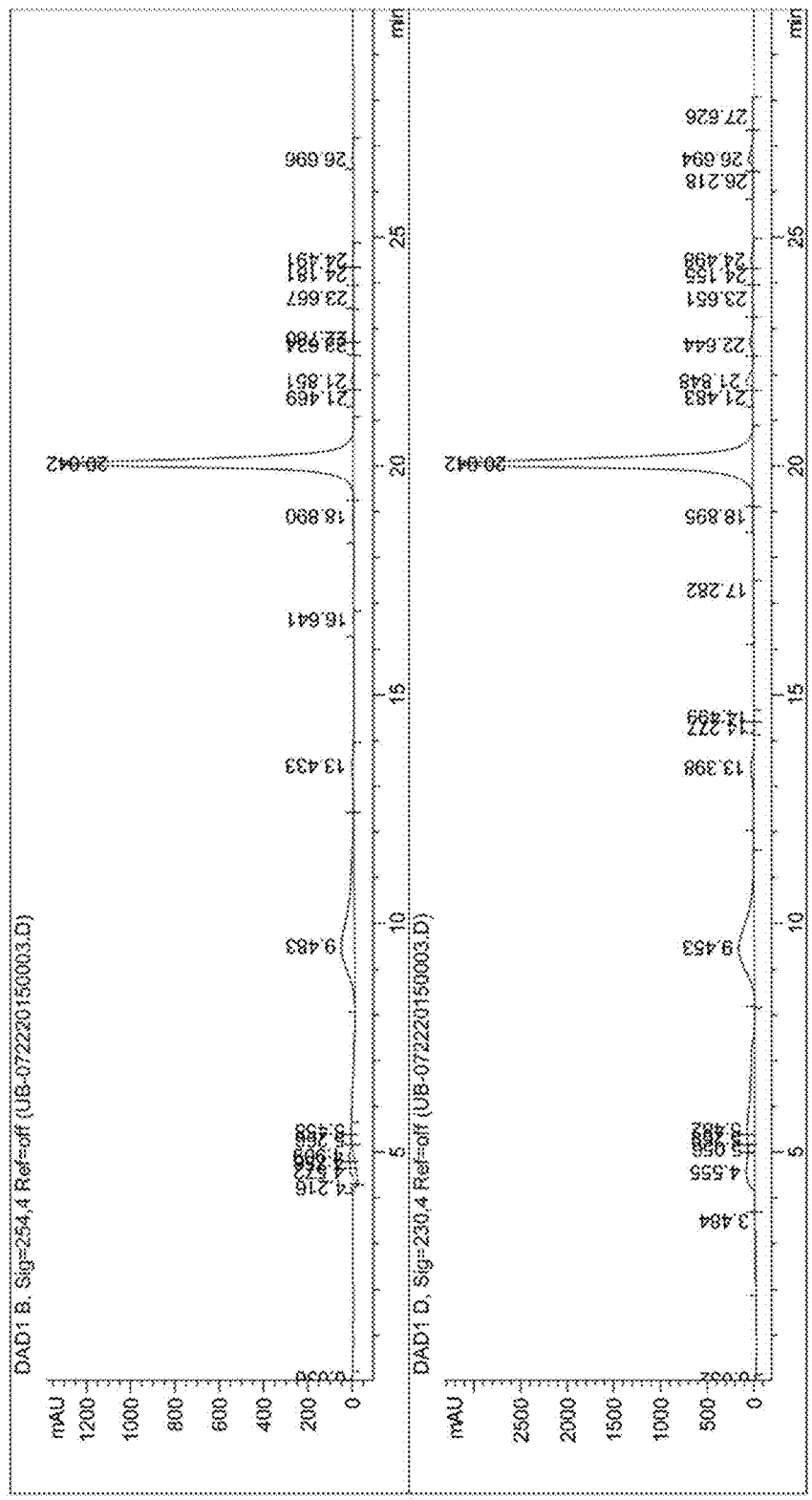
Figure 7E:
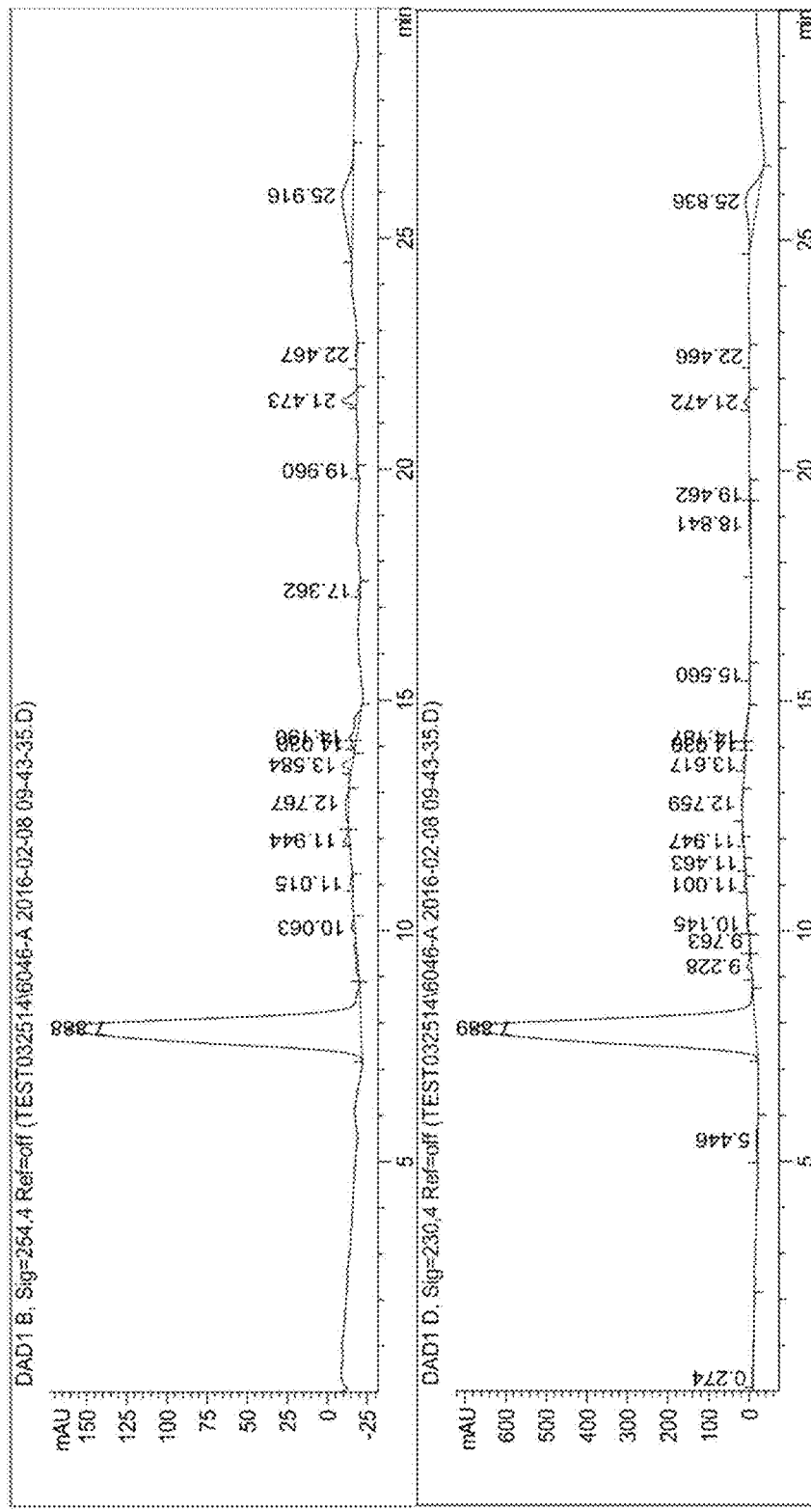

Panels A-E of FIG. 6 show selenide 1, phenol 5, acrolein, a 1:1 mixture of 1 and 5, and a 1:1 mixture of 5 and acrolein in $CD_3OD$, respectively. Upon treatment of selenide 1 with substoichiometric amounts of $H_2O_2$, both phenol 5 and acrolein were formed (Panel F of FIG. 6), supporting our proposed design for the $H_2O_2$ detection strategy.

HPLC chromatograms are shown in FIGS. 7A-E. Column specifics include: Agilent 1200 system; Flow rate: 0.6 mL/min; Max. Pressure (bar): 600. Elution conditions were as follows: $H_2O$/MeCN 95:5 to 20:80, 0-15 min; 20:80 to 0:100, 15-20 min; 0:100, 20-25 min; 0:100 to 95:5, 25-30 min. The retention time for 1 was 20.1 min, and the retention time for 5 was 27.6 min. The HPLC chromatograms include (A) authentic sample of selenide 1, (B) phenol 5, (C) selenide 1+phenol 5, (D) crude reaction mixture of selenide 1+1 equiv. $H_2O_2$, and (E) authentic sample of $PhSeO_2H$ acquired at λ=254 nm and 230 nm, respectively. FIGS. 7A-E revealed that the reaction of selenide 1 with $H_2O_2$ produced phenol 5, but did not produce $PhSeO_2H$. Therefore, pathway 1 (FIG. 2A) is operative under these conditions leading to the formation of the putative intermediate PhSeOH as a side product.

Figure 8:
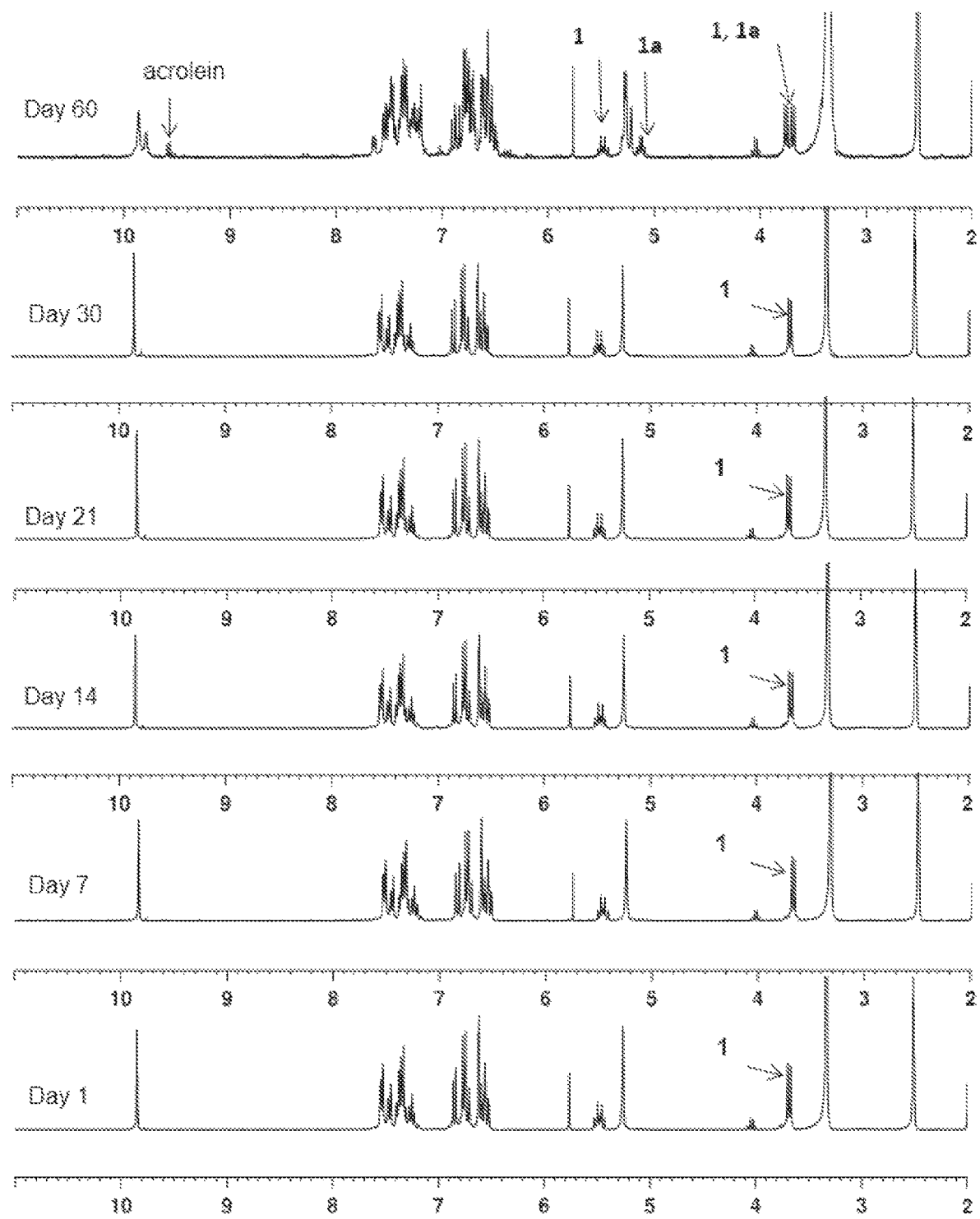
FIG. 8. $^1H$ NMR spectra (300 MHz, DMSO-$d_6$) of selenide 1 recorded on days 1, 7, 14, 21, 30, and 60.

Since organic selenides are prone to oxidation in air, the stability of 1 under ambient conditions was investigated. To study the stability of 1, the $^1H$ NMR spectra of 1 in DMSO-$d_6$ were obtained at specified intervals (days 1, 7, 14, 21, 30 and 60). The solution was left at room temperature and in air throughout the entire period. The $^1H$ NMR spectra are shown in FIG. 8. As shown in FIG. 8, acrolein, selenide 1, and compound 1a, i.e.,

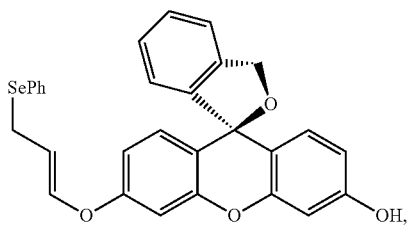

Figure 9:
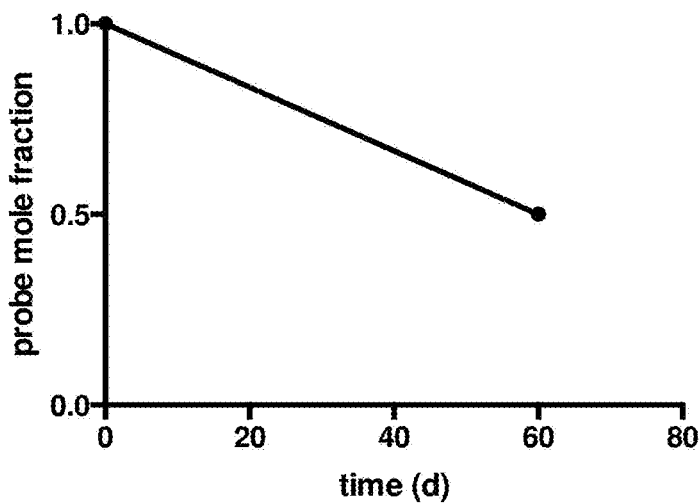
FIG. 9. Plot of the half-life of probe 1.

Ia were observed. The $^1H$ NMR analysis of 1 in [$D_6$]DMSO, as shown in FIG. 8 and the half-life graph in FIG. 9, showed that 1 underwent cis-trans isomerization of the enol ether with a half-life of 60 days. Even so, the compound was quite resistant to oxidative decomposition up to 60 days as manifested by the presence of only less than 10% acrolein.

Figure 10:
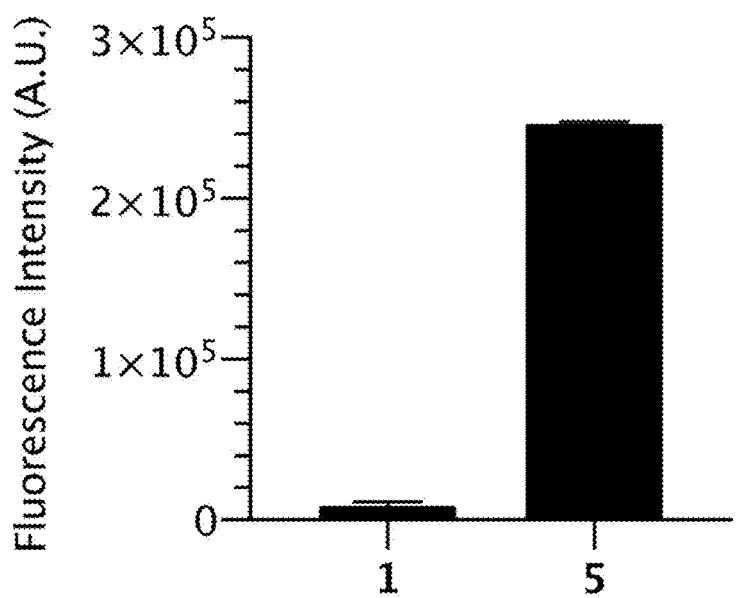
FIG. 10. Graph of the difference in fluorescence intensity between selenide 1 and phenol 5.

The fluorescence intensity of selenide 1 and phenol 5 were investigated. Solutions containing ultrapure water (681 μL), 1.2 M phosphate pH 7 buffer (31 μL), DMSO (28.1 μL), and 80 μM 1 or phenol 5 in DMSO (9.4 μL) were made. Aliquots of these solutions (200 μL) were transferred to the wells of a black 96-well plate and the fluorescence was measured. The florescence measurements for selenide 1 and phenol 5 are shown in FIG. 10, as well as tabulated in Table 1. As evident from FIG. 10 and Table 1, the difference in fluorescence intensity of probe 1 and phenol 5, is 27-fold. Generally, O-alkylation of Pittsburgh Green suppresses the fluorescence by 200-400 fold. The somewhat modest fluorescence increase in the current system is attributed to the trace contamination of the fluorescent compound 5 during the purification of the nonfluorescent probe 1.

TABLE 1

| Florescence values (n = 3) | | | |
|---|---|---|---|
| Compound | Fluorescence Intensity | | |
| 1 | 7,053 | 11,524 | 8,556 |
| 5 | 244,687 | 247,204 | 246,848 |

Figure 11:
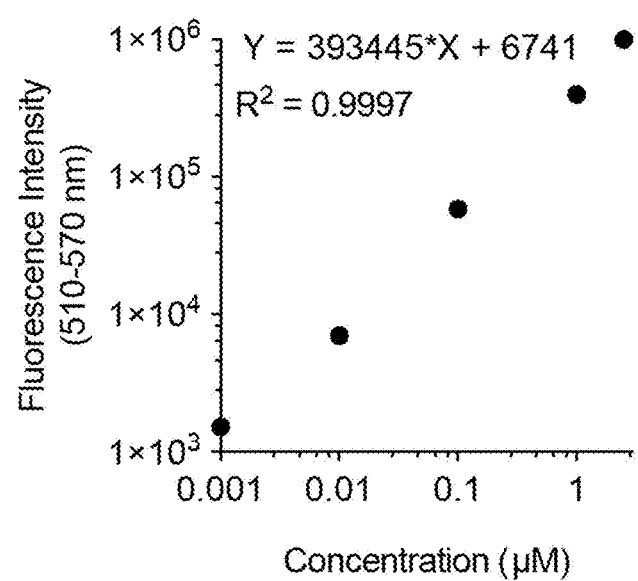
FIG. 11. Plot of the calibration curve for phenol 5 shown on a log scale 200 µL, 5% MeCN in 50 mM pH 7.5 HEPES buffer.

From the standard calibration curve shown in FIG. 11, the estimated amount of 5 in 1 as an impurity was calculated to be 2.5%, leading to a 5-10 times higher background signal. The calibration curve is shown on a log scale: 200 μL, 5% MeCN in 50 mM pH 7.5 HEPES buffer, n=2. The error bars in FIG. 11 are invisible because they are smaller than the dots. The specifics of the plotted calibration curve are shown below in Table 2.

TABLE 2

| Calibration curve of FIG. 8 | |
|---|---|
| Best-fit values | |
| Slope | 393445 ± 2396 |
| Y-intercept when X = 0.0 | 6741 ± 2887 |
| X-intercept when Y = 0.0 | −0.01713 |
| 1/slope | 2.54E−06 |
| 95% Confidence Intervals | |
| Slope | 387921 to 398969 |
| Y-intercept when X = 0.0 | 84.06 to 13397 |
| X-intercept when Y = 0.0 | −0.03434 to −0.0002119 |
| Goodness of Fit | |
| R square | 0.9997 |
| Sy · x | 7307 |
| Is slope significantly non-zero? | |
| F | 26975 |
| DFn, DFd | 1.000, 8.000 |
| P value | <0.0001 |
| Deviation from zero? | Significant |
| Data | |
| Number of X values | 5 |
| Maximum number of Y replicates | 2 |
| Total number of values | 10 |
| Number of missing values | 0 |
| Equation | Y = 393445*X + 6741 |

Thus, if trace phenol 5 can be removed from selenide 1 (HPLC did not improve the purity of 1), the signal increase in the conversion of 5 to 1 should be 125-250 fold. Nevertheless, the trace amount of 5 in 1 does not affect the calculation of rate constant shown below (FIG. 12A).

Figure 12A:
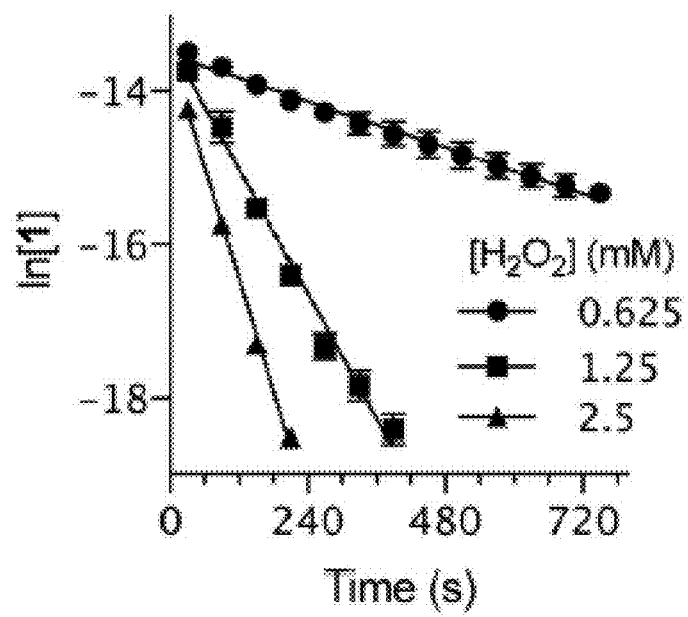
FIGS. 12A-B. A) plot of ln [1] vs. t to obtain slope (k') and B) plot of [1] vs. time. For (A), Y=−0.002514X−13.52 ($R^2$=0.8939) for 0.625 mM $H_2O_2$, Y=−0.01359X−13.38 ($R^2$=0.9792) for 1.25 mM $H_2O_2$, and Y=−0.02432X−13.51 ($R^2$=0.9978) for 2.5 mM $H_2O_2$.

With the fluorescence values and the fluorometrically measured concentrations of selenide 1 shown in Table 3 and Table 4, respectively, ln[1] versus time (s) was plotted to obtain observed rate constants k' as the slope of the linear plot (FIG. 12A). To determine the second-order rate constant of the reaction of 1 with $H_2O_2$, a solution of 1 in 5% MeCN in a pH 7.5 HEPES buffer 50 mM was treated with $H_2O_2$ in a 96-well plate, and the progressive increase in fluorescence was recorded measured every minute until the reaction was completed. Rate was determined with rate=k'[1], wherein k'=k[$H_2O_2$]. Final concentrations included: [$H_2O_2$]=0.625 mM, 1.25 mM, and 2.5 mM, as well as [1]=1.7 μM. The fluorescence readout was converted to the amount of phenol 5 formed using FIG. 8 using fluorescence intensity=393445*[5]+6741; $R^2$=0.9997.

TABLE 3

| | Fluorescence values of 1 ($F_0$ = 24616 units) | | | | | | | | |
|---|---|---|---|---|---|---|---|---|---|
| Time | $F-F_0$ (515 nm); [$H_2O_2$] = 0.625 mM | | | $F-F_0$ (515 nm); [$H_2O_2$] = 1.25 mM | | | $F-F_0$ (515 nm); [$H_2O_2$] = 2.5 mM | | |
| (s) | Expt. 1 | Expt. 2 | Expt. 3 | Expt. 1 | Expt. 2 | Expt. 3 | Expt. 1 | Expt. 2 | Expt. 3 |
| 30 | 145,691 | 101,161 | 83,026 | 255,659 | 258,915 | 225,047 | 425,024 | 405,551 | 398,309 |
| 90 | 220,196 | 277,036 | 236.883 | 364,712 | 517,271 | 484,926 | 539,467 | 612,814 | 630,136 |
| 150 | 301,900 | 391,059 | 348,470 | 463,364 | 607,290 | 590,662 | 601,940 | 657,981 | 671,943 |
| 210 | 355,049 | 458,596 | 422,910 | 514,663 | 641,798 | 639,332 | 627,168 | 666,435 | 680,181 |
| 270 | 390,358 | 499,861 | 473,964 | 549,297 | 656,229 | 660,178 | 636,230 | 665,190 | 679,336 |
| 330 | 421,561 | 522,358 | 509,584 | 572,635 | 661,539 | 664,254 | 638,753 | 666,173 | 674,138 |
| 390 | 450,025 | 534,705 | 536,252 | 589,797 | 665,178 | 666,753 | 641,141 | 663,899 | 664,993 |
| 450 | 477,638 | 541,922 | 555,207 | 601,493 | 663,842 | 669,367 | 640,270 | 661,893 | 664,413 |
| 510 | 501,767 | 546,290 | 569,868 | 606,377 | 663,608 | 673,539 | 639,383 | 659,509 | 664,003 |
| 570 | 524,121 | 550,122 | 581,518 | 612,207 | 662,594 | 675,671 | 637,346 | 658,746 | 663,104 |
| 630 | 543,908 | 551,490 | 591,076 | 614,405 | 663,947 | 677,477 | 637,422 | 656,826 | 661,222 |
| 690 | 559,985 | 551,741 | 599,176 | 616,203 | 663,123 | 679,640 | 636,174 | 654,911 | 659,002 |
| 750 | 570,897 | 553,475 | 603,780 | 616,371 | 663,595 | 679,888 | 634,294 | 654,494 | 657,410 |
| 810 | 580,693 | 553,568 | 609,902 | 614,783 | 663,765 | 683,016 | 631,953 | 653,606 | 654,988 |
| 870 | 587,536 | 552,326 | 614,108 | 614,819 | 662,173 | 685,799 | 631,346 | 651,140 | 655,338 |

TABLE 4

| | Concentration of [1] | | | | | | | | |
|---|---|---|---|---|---|---|---|---|---|
| Time | [1] µM [$H_2O_2$] = 0.625 mM | | | [1] µM [$H_2O_2$] = 1.25 mM | | | [1] µM [$H_2O_2$] = 2.5 mM | | |
| (s) | Exp. 1 | Exp. 2 | Exp. 3 | Exp. 1 | Exp. 2 | Exp. 3 | Exp. 1 | Exp. 2 | Exp. 3 |
| 30 | 1.3453 | 1.4596 | 1.5061 | 1.0631 | 1.0547 | 1.1417 | 0.6285 | 0.6785 | 0.6971 |
| 90 | 1.1541 | 1.0082 | 1.1113 | 0.7833 | 0.3918 | 0.4748 | 0.3348 | 0.1466 | 0.1022 |
| 150 | 0.9444 | 0.7157 | 0.8249 | 0.5301 | 0.1608 | 0.2035 | 0.1745 | 0.0307 | −0.005 |
| 210 | 0.8081 | 0.5424 | 0.6339 | 0.3985 | 0.0722 | 0.0786 | 0.1098 | 0.0090 | −0.026 |
| 270 | 0.7175 | 0.4365 | 0.5029 | 0.3096 | 0.0352 | 0.0251 | 0.0865 | 0.0122 | −0.024 |
| 330 | 0.6374 | 0.3787 | 0.4115 | 0.2497 | 0.0216 | 0.0146 | 0.0801 | 0.0097 | −0.010 |
| 390 | 0.5643 | 0.3470 | 0.3431 | 0.2057 | 0.0122 | 0.0082 | 0.0739 | 0.0155 | 0.0127 |
| 450 | 0.4935 | 0.3285 | 0.2944 | 0.1757 | 0.0157 | 0.0015 | 0.0762 | 0.0207 | 0.0142 |
| 510 | 0.4316 | 0.3173 | 0.2568 | 0.1631 | 0.0163 | −0.009 | 0.0784 | 0.0268 | 0.0153 |
| 570 | 0.3742 | 0.3075 | 0.2269 | 0.1482 | 0.0189 | −0.014 | 0.0837 | 0.0288 | 0.0176 |
| 630 | 0.3234 | 0.3040 | 0.2024 | 0.1425 | 0.0154 | −0.019 | 0.0835 | 0.0337 | 0.0224 |
| 690 | 0.2822 | 0.3033 | 0.1816 | 0.1379 | 0.0175 | −0.024 | 0.0867 | 0.0386 | 0.0281 |
| 750 | 0.2542 | 0.2989 | 0.1698 | 0.1375 | 0.0163 | −0.025 | 0.0915 | 0.0397 | 0.0322 |
| 810 | 0.2290 | 0.2986 | 0.1541 | 0.1416 | 0.0159 | −0.033 | 0.0975 | 0.0419 | 0.0384 |
| 870 | 0.2115 | 0.3018 | 0.1433 | 0.1415 | 0.0200 | −0.040 | 0.0991 | 0.0483 | 0.0375 |

Figure 12B:
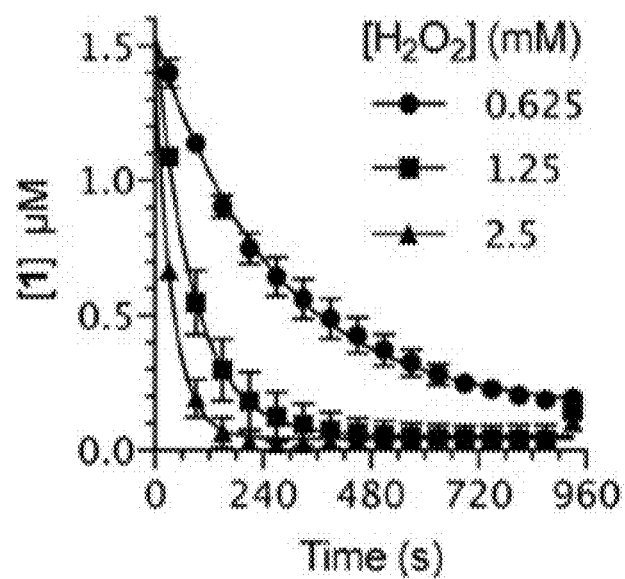
Figure 13:
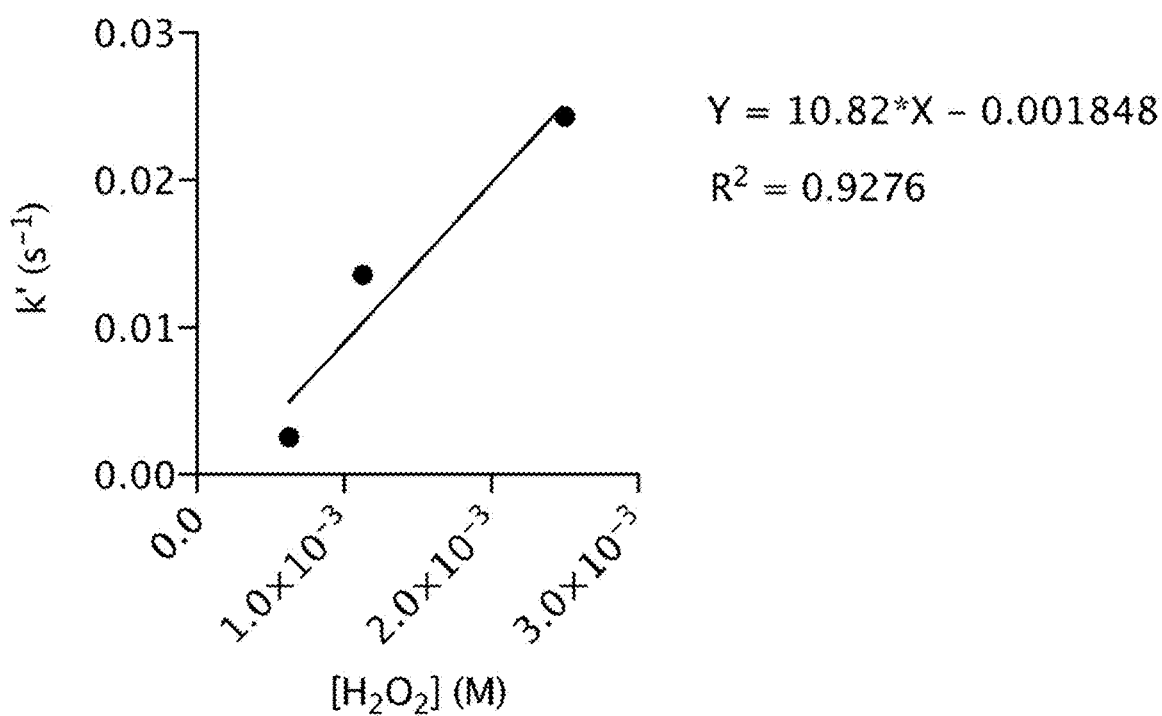
FIG. 13. Plot of k' versus concentration of $H_2O_2$ to obtain second order rate constant k.

From FIG. 12B, three values of k' were obtained for three different concentrations of $H_2O_2$, which are shown below in Table 5. Based on the pseudo first-order kinetic studies (FIG. 12B), the second-order rate constant k of the reaction was determined by plotting the observed rate constant k' versus [1$H_2O_2$] yielding the second rate constant as the slope of the linear plot. The second order rate constant was calculated using FIG. 13 and Table 4 to be k=9.82±1.11 $m^{-1}s^{-1}$.

TABLE 5

| Slope (k') from the FIG. 12A | |
|---|---|
| [$H_2O_2$] (mM) | Slope k' ($s^{-1}$) |
| 2.5 | 0.02432 |
| 1.25 | 0.01359 |
| 0.625 | 0.00251 |

To verify that 1 could quantitatively measure $H_2O_2$ concentrations, 1 was incubated with increasing concentrations of $H_2O_2$. A solution of 0-159 µM $H_2O_2$ in 5:95 MeCN/50 mM phosphate pH 7 buffer (180 µL) was added to the wells of a black 96-well plate. A solution of 100 µM 1 in MeCN (20 µL) was then added to the wells. The solutions were allowed to incubate at 25° C. for 20 min before the fluorescence was measured. Fluorescence increased linearly with $H_2O_2$ concentration (FIG. 14A), indicating that the probe could be used to quantify $H_2O_2$.

Figure 15:
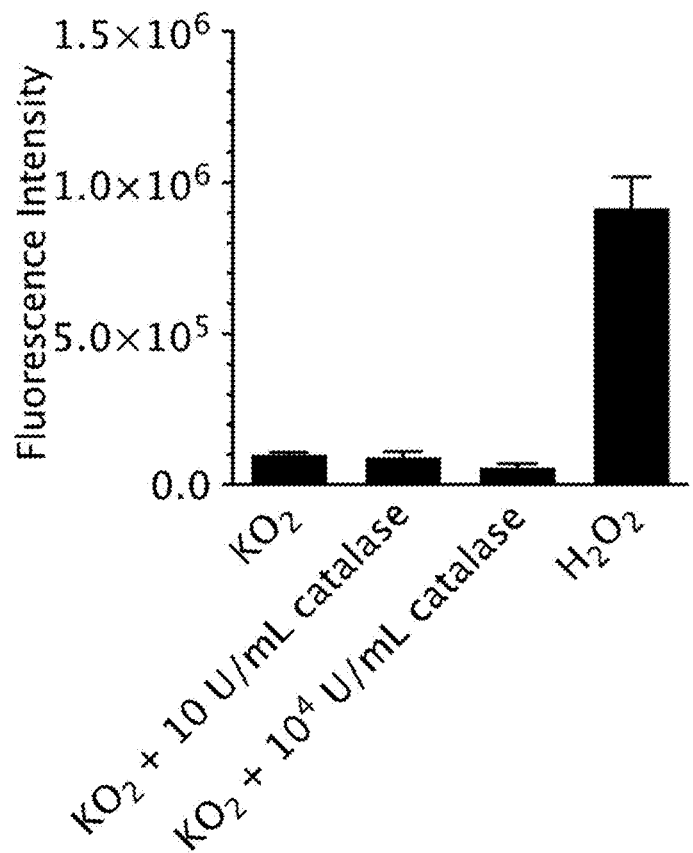
FIG. 15. Graph of the fluorescence intensity of 1 with potassium superoxide, and with catalase added in some tests, to investigate the selectivity of 1 reacted with $O_2^{\bullet-}$.

Following the concentration dependence studies, the selectivity of 1 was assessed against $O_2^{•-}$, $^1O_2$, •OH, ClO⁻, ONOO⁻, $^tBuOOH$, $NO_3^-$, $NO_2$, and NO•. Relative to $H_2O_2$, little reaction was observed with other ROS and RNS (FIG. 14B). The production of some of these ROS required $H_2O_2$ as a reagent or generated $H_2O_2$ as a product, for which we carefully performed control experiments as detailed below. For example, a solution of 100 µM 1 in ethanol (20 µL) was added to 5:95 methanol/50 mM phosphate pH 7 buffer (140 µL). Since $O_2^{•-}$ is known to spontaneously dismutate to form $H_2O_2$, either 0, 10, or 104 U/mL catalase (20 µL) was added to the mixtures to ensure that 1 did not react with any of the in situ-generated $H_2O_2$. A control containing 100 µM 1 in ethanol (20 µL), 5:95 methanol/50 mM phosphate pH 7 buffer (160 µL), and 700 mM $H_2O_2$ (20 µL) was also generated. The solutions were allowed to incubate at 25° C. for 15 min prior to measuring fluorescence. Selenide 1 reacted readily with $H_2O_2$, while the observed fluorescence from the samples containing $KO_2$ decreased with increasing catalase concentrations (FIG. 15 and Table 6), indicating that 1 did not react with $O_2^{•-}$. Therefore, 1 is selective for $H_2O_2$ over $O_2^{•-}$.

TABLE 6

Fluorescence values for determining
selectivity of 1: reaction with $O_2^-$ (n = 3)

| Sample | Fluorescence Intensity | | |
|---|---|---|---|
| $KO_2$ | 106,099 | 92,938 | 99,300 |
| $KO_2$ + 10 U/mL catalase | 104,768 | 72,151 | 98,514 |
| $KO_2$ + $10^4$ U/mL catalase | 63,553 | 41,950 | 67,009 |
| $H_2O_2$ | 937,451 | 1,008,330 | 803,382 |

Figure 16:
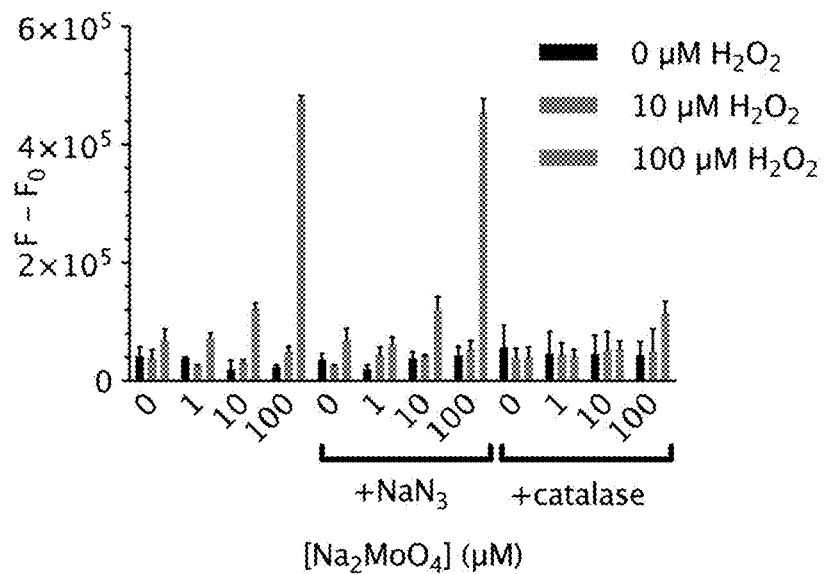
FIG. 16. Graph of the fluorescence intensity of 1 with $NaMoO_4$, with $NaN_3$ or catalase added in some tests, to investigate the selectivity of 1 reacted with $^1O_2$.

Probe 1 was titrated with $NaMoO_4$ and $H_2O_2$ to determine whether $^1O_2$ reacted with the probe 1. A solution of 100 µM 1 in ethanol (20 µL) was added to 5:95 methanol/50 mM phosphate pH 7 buffer (140 µL). Water, 1 mM sodium azide, or $10^4$ U/mL catalase (20 µL) was added to the mixture. $NaMoO_4 \cdot 2H_2O$ (11.1 mg) was added to ultrapure water (2.00 mL). This solution was diluted to 20 µM, 200 µM, and 2.00 mM. $H_2O_2$ was diluted to 200 µM and 2.00 mM. Equal volumes of $NaMoO_4$ solution and $H_2O_2$ were added together, and an aliquot (20 µL) was immediately transferred to the solution containing 1. The fluorescence intensity was measured immediately and again after incubation at 25° C. for 40 min. A large fluorescence increase was observed only in the samples containing 100 mm of both $Na_2MoO_4$ and $H_2O_2$(FIG. 16 and Table 7). Fluorescence did not increase in samples containing only $Na_2MoO_4$, indicating that the probe was not reacting with the $Na_2MoO_4$. Together, these results suggested that the probe may have reacted with $^1O_2$. However, the addition of $NaN_3$, a known $^1O_2$ scavenger, did not decrease the fluorescence. Thus, it was concluded that the fluorescence increase was caused by the $H_2O_2$ required to produce $^1O_2$ and not by $^1O_2$ itself. $10^4$ $UmL^{-1}$ catalase was added to the solutions to verify that 1 indeed responded to excess $H_2O_2$ that had not reacted with the $Na_2MoO_4$. The addition of catalase abolished the fluorescence signal observed in the presence of high concentrations of $H_2O_2$ (FIG. 16 and Table 7). The fluorescence values in Table 7 are the fluorescence at 40 min minus the fluorescence at 0 min.

TABLE 7

Fluorescence values for determining selectivity of 1: Reaction with $^1O_2$ (n = 3)

| Additive | [NaMoO₄] (µM) | 0 µM $H_2O_2$ | | | 10 µM $H_2O_2$ | | | 100 µM $H_2O_2$ | | |
|---|---|---|---|---|---|---|---|---|---|---|
| | 0 | 59,711 | 30,413 | 38,407 | 34,413 | 26,177 | 54,164 | 86,970 | 68,803 | 48,948 |
| | 1 | 36,829 | 38,478 | 40,456 | 27,103 | 23,437 | 25,142 | 74,322 | 79,262 | 64,673 |
| | 10 | 1,067 | 29,637 | 27,490 | 33,243 | 34,233 | 26,543 | 132,450 | 119,014 | 113,217 |
| | 100 | 24,734 | 26,617 | 17,702 | 38,768 | 55,874 | 53,722 | 476,166 | 482,448 | 468,686 |
| $NaN_3$ | 0 | 47,427 | 27,816 | 33,822 | 22,037 | 25,574 | 26,509 | 47,879 | 71,128 | 86,779 |
| $NaN_3$ | 1 | 17,056 | 15,590 | 28,737 | 47,687 | 30,921 | 55,460 | 58,618 | 52,801 | 75,276 |
| $NaN_3$ | 10 | 48,985 | 26,189 | 39,286 | 41,011 | 44,837 | 41,481 | 99,199 | 137,922 | 128,720 |
| $NaN_3$ | 100 | 41,150 | 60,360 | 31,422 | 36,764 | 62,417 | 61,596 | 459,433 | 473,881 | 427,359 |
| catalase | 0 | 47,781 | 25,839 | 97,988 | 24,872 | 37,852 | 55,740 | 24,774 | 36,194 | 57,786 |
| catalase | 1 | 32,277 | 18,911 | 88,941 | 25,228 | 47,957 | 62,449 | 34,302 | 31,904 | 54,776 |
| catalase | 10 | 30,189 | 24,960 | 82,044 | 31,421 | 39,031 | 88,171 | 39,161 | 54,221 | 66,499 |
| catalase | 100 | 27,512 | 34,883 | 69,835 | 25,678 | 32,090 | 94,073 | 103,725 | 102,097 | 137,047 |

Figure 17:
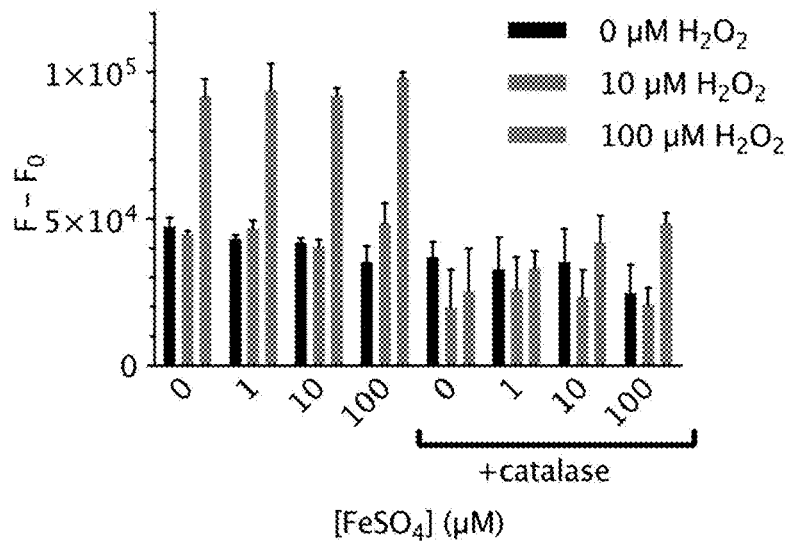
FIG. 17. Graph of the fluorescence intensity of 1 with $FeSO_4 \cdot 7H_2O$, and with catalase added in some tests, to investigate the selectivity of 1 reacted with •OH.

The reactivity of 1 with •OH was also investigated. •OH was generated through the reaction of $FeSO_4 \cdot 7H_2O$ with $H_2O_2$. A solution of 100 µM 1 in ethanol (20 µL) was added to 5:95 methanol/50 mM phosphate pH 7 buffer (140 µL). Water or 104 U/mL catalase (20 µL) was added to the mixture. $FeSO_4 \cdot 7H_2O$ (27.4 mg) was added to ultrapure water (2.00 mL). This solution was diluted to 20 µM, 200 µM, and 2.00 mM. $H_2O_2$ was diluted to 200 µM and 2.00 mM. Equal volumes of $FeSO_4 \cdot 7H_2O$ solution and $H_2O_2$ were added together, and an aliquot (20 µL) was immediately transferred to the solution containing 1. The fluorescence intensity was measured immediately and again after incubation at 25° C. for 40 min. Fluorescence did not increase as the concentration of $FeSO_4$ increased (FIG. 17 and Table 8), indicating that neither $FeSO_4$ nor the •OH reacted with the probe. Addition of catalase to the solution reduced fluorescence intensity, indicating that the enhanced signals were caused by the reaction of the probe with the $H_2O_2$ required to produce •OH. The Fluorescence values in Table 8 are the fluorescence at 40 min minus the fluorescence at 0 min.

TABLE 8

Fluorescence values for determining selectivity of 1: Reaction with •OH (n = 3)

| Additive | [FeSO₄] (µM) | 0 µM $H_2O_2$ | | | 10 µM $H_2O_2$ | | | 100 µM $H_2O_2$ | | |
|---|---|---|---|---|---|---|---|---|---|---|
| | 0 | 50,173 | 48,124 | 44,143 | 43,929 | 46,186 | 43,989 | 94,742 | 95,713 | 85,271 |
| | 1 | 44,775 | 42,847 | 41,775 | 49,425 | 47,262 | 44,251 | 103,905 | 91,684 | 86,594 |
| | 10 | 43,299 | 42,365 | 40,214 | 42,933 | 40,908 | 38,283 | 90,712 | 94,948 | 91,049 |
| | 100 | 32,709 | 41,651 | 31,615 | 56,260 | 46,281 | 43,358 | 99,391 | 95,778 | 99,384 |

TABLE 8-continued

Fluorescence values for determining selectivity of 1: Reaction with •OH (n = 3)

| Additive | [FeSO$_4$] (μM) | 0 μM H$_2$O$_2$ | | | 10 μM H$_2$O$_2$ | | | 100 μM H$_2$O$_2$ | | |
|---|---|---|---|---|---|---|---|---|---|---|
| catalase | 0 | 31,506 | 41,640 | 38,159 | 16,840 | 33,959 | 8,517 | 37,819 | 28,926 | 9,145 |
| catalase | 1 | 28,688 | 24,659 | 45,310 | 31,319 | 13,633 | 33,399 | 34,591 | 26,790 | 38,285 |
| catalase | 10 | 24,822 | 33,920 | 47,376 | 19,991 | 16,693 | 33,776 | 42,724 | 50,635 | 32,300 |
| catalase | 100 | 35,828 | 18,194 | 20,321 | 20,486 | 26,765 | 15,423 | 46,921 | 52,666 | 46,232 |

Figure 18:
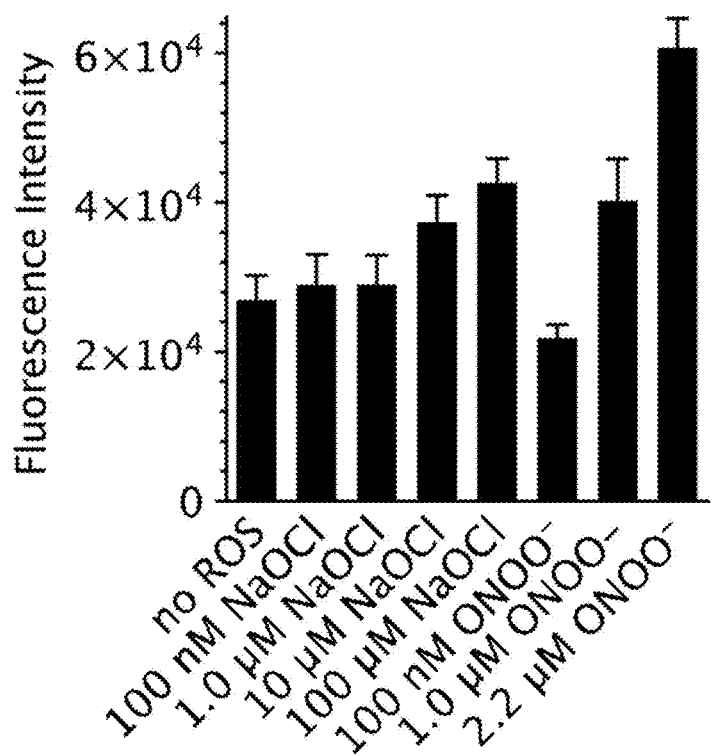
FIG. 18. Graph of the fluorescence intensity of 1 with $ONOO^-$ or NaOCl to investigate the selectivity of 1 reacted with $ONOO^-$ or $ClO^-$, respectively.

Next, it was tested whether OCl⁻ and ONOO⁻ (peroxynitrite), would react with 1. A solution of 0, 1, 10, or 22 μM ONOO— in 0.3 M NaOH (20 μL) or 1, 10, 100, or 1000 μM NaOCl in water (20 μL) was added to the wells of a black 96-well plate. A solution of 10 μM 1 in DMSO (560 μL) and 5:95 MeCN/1.2 M phosphate pH 7 buffer (4.48 mL) was made; this solution (180 μL) was transferred to each of the wells. The samples were allowed to incubate at 25° C. for 15 min before the fluorescence was measured. No statistically significant increase in fluorescence intensity was observed with increasing concentrations of OCl⁻. A slight increase in fluorescence intensity was observed with increasing ONOO⁻ concentration (FIG. 18 and Table 9). This may be attributed to trace amounts of H$_2$O$_2$ in the ONOO⁻ solution. Furthermore, ONOO⁻ may be too unstable to last and react with 1 under aqueous conditions because, once protonated, ONOO⁻ has only a half-life of 1.9 s at pH 7.4.

TABLE 9

Fluorescence values for determining selectivity of 1: Reaction with ClO⁻ and ONOO⁻ (n =3)

| | Fluorescence Intensity | | |
|---|---|---|---|
| no ROS | 30,591 | 24,478 | 26,025 |
| 100 nM NaOCl | 33,503 | 25,413 | 28,088 |
| 1.0 μM NaOCl | 28,551 | 25,590 | 33,211 |
| 10 μM NaOCl | 41,611 | 35,271 | 35,308 |
| 100 μM NaOCl | 46,362 | 40,070 | 41,695 |
| 100 nM ONOO⁻ | 23,606 | 21,961 | 20,229 |
| 1.0 μM ONOO⁻ | 46,271 | 39,358 | 35,209 |
| 2.2 μM ONOO⁻ | 63,954 | 56,351 | 61,987 |

Figure 19:
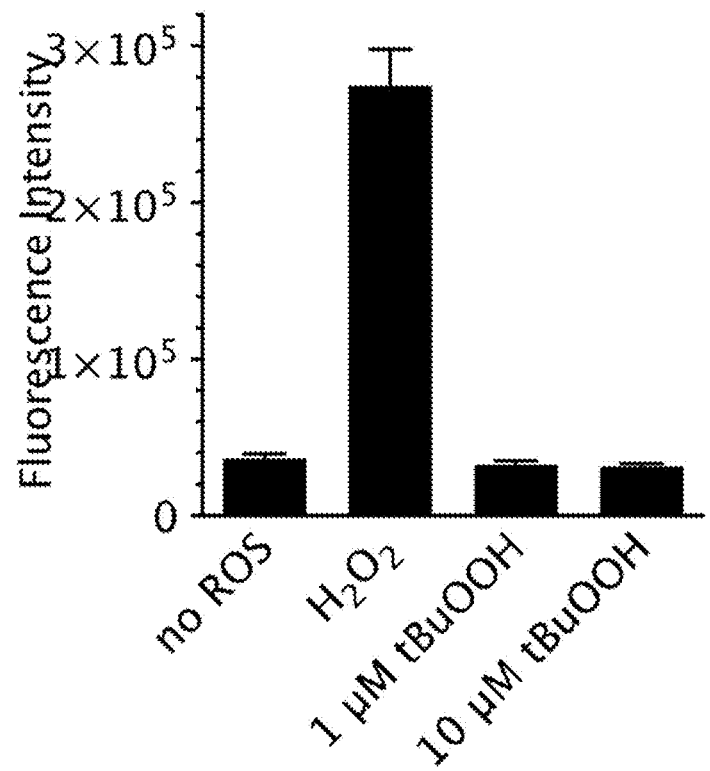
FIG. 19. Graph of the fluorescence intensity of 1 with ′BuOOH to investigate the selectivity of 1 reacted with ′BuOOH.

'BuOOH was also tested for reactivity with 1. A solution of 5:95 MeCN/50 mM phosphate pH 7 buffer (160 μL) was added to the wells of a black 96-well plate. 10 μM 1 in DMSO (20 μL) was added to each well. 0 mM H$_2$O$_2$ in water (20 μL) or 0, 10, or 100 μM tBuOOH in DMSO (20 μL) were then added to the wells. The samples were allowed to incubate at 25° C. for 15 min before the fluorescence was measured. 'BuOOH did not produce fluorescence even at 10 μM (FIG. 19 and Table 10). The minute or negligible fluorescence signals observed in these studies led us to conclude that the tested ROS do not interfere with the 1-based fluorometric method for H$_2$O$_2$.

TABLE 10

Fluorescence values for determining selectivity of 1: Reaction with 'BuOOH (n = 3)

| | Fluorescence Intensity | | |
|---|---|---|---|
| no ROS | 34,525 | 36,401 | 39,836 |
| H$_2$O$_2$ | 277,013 | 296,506 | 250,145 |
| 1 μM 'BuOOH | 32,951 | 29634 | 34,860 |
| 10 μM 'BuOOH | 31,650 | 28,922 | 33,363 |

It was then sought to determine whether RNS would react with 1 to produce fluorescence. The probe 1 was first exposed to NO$_2$⁻ at various concentrations. NaNO$_2$ (97.0 mg) was dissolved in ultrapure water (2.00 mL). This solution was diluted to 10 μM, 100 μM, 1.00 mM, and 10.0 mM. H$_2$O$_2$ was diluted to 10 μM, 100 μM, 1.00 mM, and 10.0 mM. A solution of 100 μM 1 in ethanol (20 μL) was added to 5:95 methanol/50 mM phosphate pH 7 buffer (160 μL). The NaNO$_2$ or H$_2$O$_2$ solutions (20 μL) were added to the solution containing 1 and the fluorescence intensity was measured immediately and again after incubation at 25° C. for 15 min. The fluorescence change over the first 15 min was reported for NO$_2$⁻ in FIG. 20 and Table 11.

TABLE 11

Fluorescence values for determining selectivity of 1: Reaction with NO$_2$⁻ (n = 3)

| [NO$_2$⁻] or [H$_2$O$_2$] (μM) | NO$_2$⁻ | | | H$_2$O$_2$ | | |
|---|---|---|---|---|---|---|
| 0 | 24,359 | 26,870 | 26,226 | | | |
| 0.1 | 31,075 | 36,429 | 27,504 | 58,172 | 52,104 | 52,249 |
| 1 | 26,768 | 31,470 | 33,004 | 266,770 | 242,313 | 222,834 |

The probe 1 was then exposed to NO$_3$⁻ at various concentrations. NaNO$_3$ (30.9 mg) was dissolved in ultrapure water (2.00 mL). This solution was diluted to 10 μM, 100 μM, 1.00 mM, and 10.0 mM. H$_2$O$_2$ was diluted to 10 μM, 100 μM, 1.00 mM, and 10.0 mM. A solution of 100 μM 1 in ethanol (20 μL) was added to 5:95 methanol/50 mM pH 7 potassium phosphate buffer (160 μL). The NaNO$_3$ or H$_2$O$_2$ solutions (20 μL) were added to the solution containing 1 and the fluorescence intensity was measured immediately and again after incubation at 25° C. for 15 min. The fluorescence change over the first 15 min was reported for NO$_3$⁻ in FIG. 21 and Table 12. The fluorescence values in Table 12 are the fluorescence at 15 min minus the fluorescence at 0 min. No concentration dependence was observed with either NO$_2$⁻ or NO$_3$⁻ indicating that 1 did not react with these RNS.

TABLE 12

Fluorescence values for determining selectivity of 1: Reaction with NO$_3$⁻ (n = 3)

| [NO$_3$⁻] or [H$_2$O$_2$] (μM) | NO$_3$⁻ | | | H$_2$O$_2$ | | |
|---|---|---|---|---|---|---|
| 0 | 24,359 | 26,870 | 26,226 | | | |
| 0.1 | 34,507 | 35,439 | 40,487 | 58,172 | 52,104 | 52,249 |
| 1 | 43,966 | 35,385 | 47,433 | 266,770 | 242,313 | 222,834 |

Figure 22:
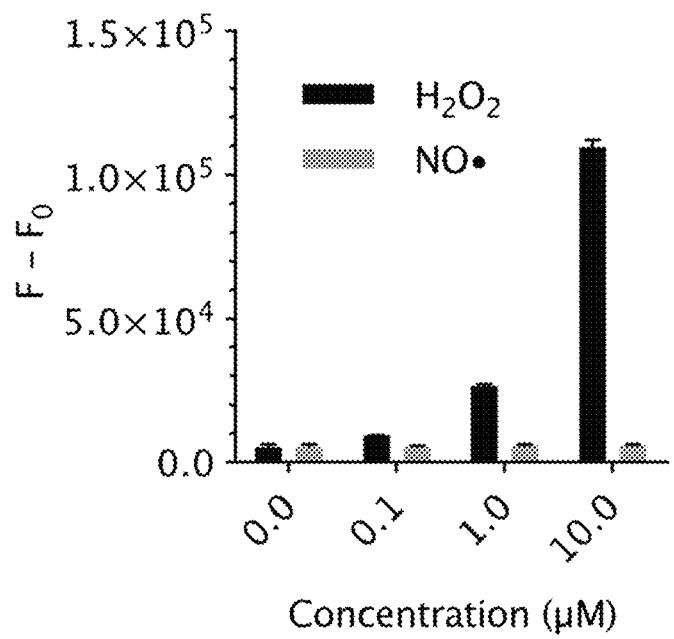
FIG. 22. Graph of the fluorescence intensity of 1 with $H_2SO_4$ added to $NaNO_2$ (to form NO•) to investigate the selectivity of 1 reacted with NO•.

The probe 1 was also exposed to NO• at various concentrations. A NO• solution was generated by the addition of H$_2$SO$_4$ to NaNO$_2$. A round-bottom flask containing a saturated solution of NaNO$_2$ was connected to a series of three bubblers and one Erlenmeyer flask; the first two bubblers contained 30% NaOH, and the third contained ultrapure water. The flask contained ultrapure water (10 mL). The solutions were degassed with argon for 30 min. Then a 2 M solution of $H_2SO_4$ (1 mL) was added to the saturated $NaNO_2$ to produce a 1.8 mM solution of NO• (assuming saturation at 25° C.) in the flask. A solution of 10 µM 1 in DMSO (20 µL) was added to 5:95 acetonitrile/50 mM pH 7 potassium phosphate buffer (160 µL). The NO• solution (20 µL) was then added to the mixture containing 1. The fluorescence was measured immediately and again after 15 min at 25° C. Similar results as the results for $NO_2^-$ and $NO_3^-$ were obtained for NO• (FIG. 22 and Table 13). The data in Table 13 is the fluorescence at 15 min minus the fluorescence at 0 min.

TABLE 13

Fluorescence values for determining of 1:
Reaction with NO• (n = 3)

| [NO•] or [$H_2O_2$] (µM) | NO• | | | $H_2O_2$ | | |
|---|---|---|---|---|---|---|
| 0 | 4,567 | 5,018 | 6,300 | | | |
| 0.1 | 5,344 | 5,827 | 5,393 | 9,370 | 9,525 | 9,517 |
| 1 | 6,268 | 5,961 | 5,430 | 26,155 | 26,618 | 27,176 |
| 10 | 6,104 | 6,207 | 5,735 | 111,008 | 106,765 | 111,053 |

Figure 20:
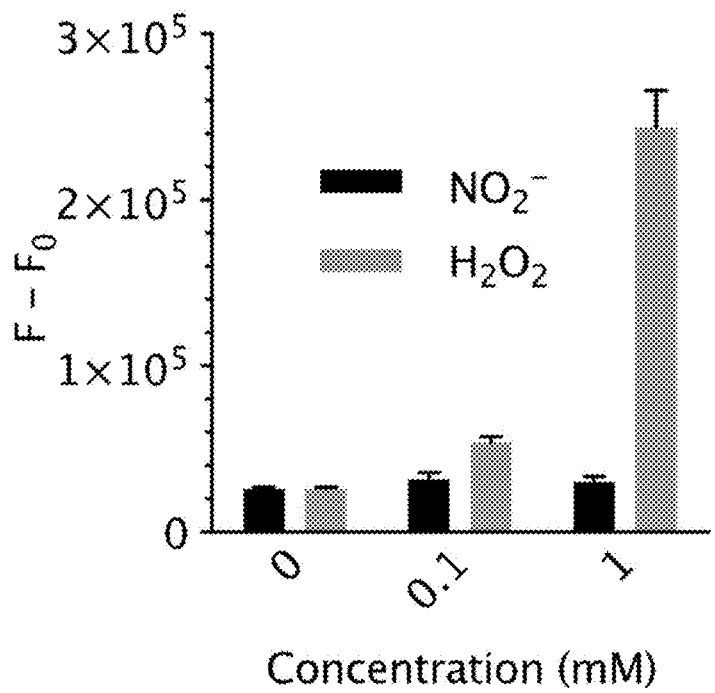
FIG. 20. Graph of the fluorescence intensity of 1 with $NaNO_2$ to investigate the selectivity of 1 reacted with $NO_2^-$.
Figure 21:
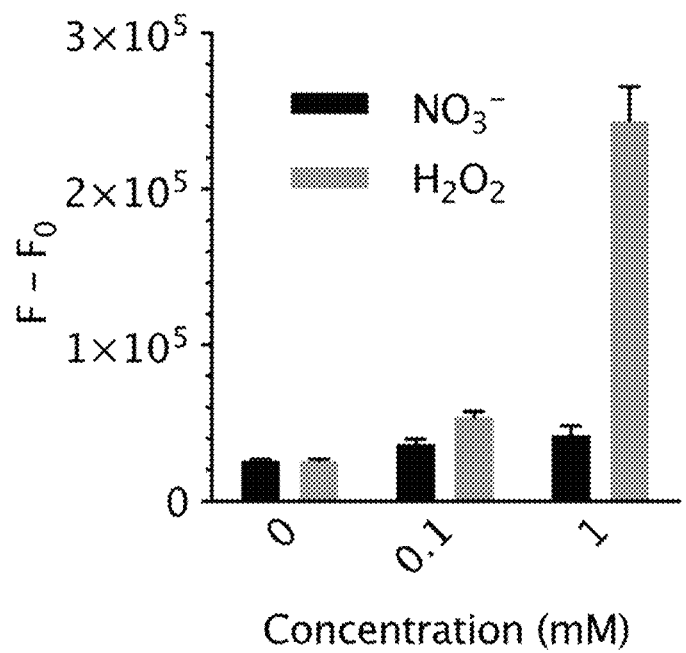
FIG. 21. Graph of the fluorescence intensity of 1 with $NaNO_3$ to investigate the selectivity of 1 reacted with $NO_3^-$.

This data in FIGS. 20-22 and Tables 11-13 suggests that 1 did not react with $NO_2^-$, $NO_3^-$, or NO•. Altogether, the fluorometric method is selective for $H_2O_2$.

The probe's response to $H_2O_2$ in the pH 4-7.3 range was studied to determine whether this technology would work in acidic and neutral intracellular environments, such as lysosomes (pH 5), Golgi apparatus (pH 6.4-6.8), mitochondria (pH 6.9-8.0), and cytoplasm (pH 7.1-7.6). A solution of 50 mM phosphate pH 7.3 buffer was treated with 1.0 N HCl to adjust the pH to 7.0, 6.5, 5.9, 5.4, 4.5, or 4.1. The concentration of the resulting buffers was adjusted with water to 25 mM phosphate buffer. Solutions of 25 mM phosphate pH 7.3, 7.0, 6.5, 5.9, 5.4, 4.5, or 4.1 buffer (160 µL) and 100 µM probe 1 in MeOH were treated with 100 µM, 10 µM or 0 µM $H_2O_2$ in water. The solutions were allowed to incubate at 23° C. for 20 min prior to measuring the fluorescence. The fluorescence values are shown in FIG. 14C and Table 14.

TABLE 14

Fluorescence values for the reaction of 1 with $H_2O_2$ at 4.1-7.3

| pH | 10 µM $H_2O_2$ | | | 1 µM $H_2O_2$ | | | 0 µM $H_2O_2$ | | |
|---|---|---|---|---|---|---|---|---|---|
| 7.30 | 372,555 | 388,584 | 401,912 | 228,368 | 208,913 | 186,665 | 189,898 | 183,424 | 169,054 |
| 7.00 | 389,464 | 369,467 | 390,006 | 247,464 | 221,499 | 229,530 | 199,101 | 207,136 | 187,676 |
| 6.50 | 332,896 | 341,948 | 335,544 | 203,661 | 188,050 | 184,986 | 155,151 | 183,747 | 149,421 |
| 5.90 | 167,836 | 187,633 | 154,515 | 113,703 | 111,368 | 107,545 | 87,499 | 89,708 | 90,424 |
| 5.40 | 103,516 | 107,311 | 103,354 | 61,365 | 63,294 | 60,943 | 56,192 | 56,334 | 52,671 |
| 4.50 | 55,577 | 54,961 | 56,315 | 40,599 | 31,790 | 3,283 | 29,770 | 29,064 | 29,069 |
| 4.10 | 51,632 | 54,097 | 52,472 | 35,884 | 30,492 | 30,471 | 28,470 | 29,037 | 28,661 |

The probe should ideally also work under oxidative stress conditions, wherein pH decreases to 6.9-7.0. It was found that the fluorescence signals were higher when the pH was above 5.4.

Figure 23:
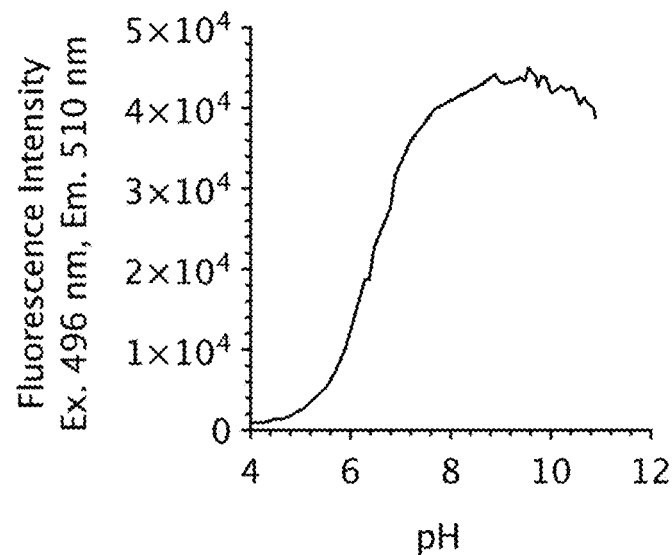
FIG. 23. Plot of the fluorescence intensity versus the pH of a phenol 5 solution.

The pH dependence of phenol 5 was also investigated. Phenol 5 was dissolved in water to a concentration of 100 nM. This solution (100 mL) was titrated with HCl and NaOH. The pH was measured after each addition before measuring the fluorescence using a Horiba FluoroMax3 fluorescence spectrometer. Fluorescence was measured using 1 nm slit widths with an excitation wavelength of 496 nm and an emission wavelength of 510 nm, the results of which are shown in FIG. 23 and Table 15.

TABLE 15

Fluorescence values for the pH dependence of hydroxymethyl Tokyo Green

| pH | Fluorescence Intensity |
|---|---|
| 3.99 | 920 |
| 4.20 | 930 |
| 4.33 | 1,070 |
| 4.48 | 1,450 |
| 4.65 | 1,440 |
| 4.77 | 1,670 |
| 5.07 | 2,790 |
| 5.51 | 5,280 |
| 5.69 | 7,130 |
| 5.90 | 10,250 |
| 6.30 | 18,790 |
| 6.38 | 18,720 |
| 6.48 | 22,820 |
| 6.80 | 27,620 |
| 6.90 | 31,730 |
| 7.11 | 34,510 |
| 7.18 | 35,740 |
| 7.69 | 39,880 |
| 8.31 | 41,950 |
| 8.63 | 42,930 |
| 8.88 | 44,240 |
| 9.00 | 43,280 |
| 9.09 | 43,110 |
| 9.15 | 43,140 |
| 9.32 | 43,550 |
| 9.40 | 43,850 |
| 9.49 | 43,340 |
| 9.56 | 45,080 |
| 9.61 | 44,640 |
| 9.71 | 43,930 |
| 9.75 | 42,610 |
| 9.83 | 44,070 |
| 9.92 | 43,670 |
| 10.01 | 41,900 |
| 10.10 | 42,170 |
| 10.22 | 42,800 |
| 10.33 | 42,170 |
| 10.43 | 42,570 |
| 10.48 | 42,410 |
| 10.59 | 40,450 |

TABLE 15-continued

Fluorescence values for the pH dependence of hydroxymethyl Tokyo Green

| pH | Fluorescence Intensity |
|---|---|
| 10.68 | 41,370 |
| 10.75 | 40,520 |

TABLE 15-continued

Fluorescence values for the pH dependence
of hydroxymethyl Tokyo Green

| pH | Fluorescence Intensity |
|---|---|
| 10.85 | 40,140 |
| 10.91 | 38,790 |

The lower signals under acidic conditions match the pH fluorescence profile of phenol 5 (FIG. 23) and are not related to efficiency of the conversion from 1 to 5. Therefore, the fluorescence method is effective in most of the biologically relevant pH range.

Figure 24A:
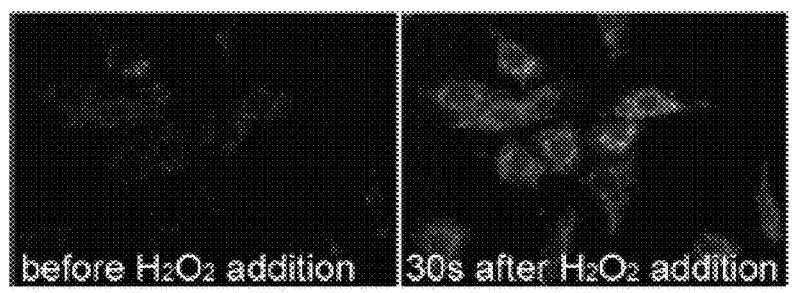
FIGS. 24A-D. Cellular images using 1. A) HeLa cells treated with 1 showed a significant fluorescence increase after the addition of $H_2O_2$. Cells were loaded with 1 for 15 min and washed prior to imaging. $H_2O_2$ was added while imaging. B) RAW macrophages loaded with 0.5 μM 1 showed (C) a significant response within 30 s of addition of ionomycin (final concentration: 10 μM). Fluorescence channel (green) and pseudo-color shown. D) Endothelial cells loaded with 1 and MitoTracker Red were stimulated with ionomycin (final concentration: 10 μM). Colocalization studies revealed mildly increased green fluorescence intensity in mitochondria.

It was then attempted to image $H_2O_2$ within cells. HeLa cells were seeded on 35-mm glass bottom dishes (MatTek Corporation, Ashland, MA) and incubated with 0.5 µM 1 in 0.1% DMSO in DMEM (10% FBS with penicillin/streptomycin) prior to imaging. After washing with HBSS and replacing the media, $H_2O_2$ was added. The dish was inserted in a closed, thermo-controlled (37° C.) stage top incubator (Tokai Hit Co., Shizuoka-ken, Ja-pan) atop the motorized stage of an inverted Nikon TiE fluorescent microscope (Nikon Inc., Melville, NY) equipped with a 60× oil immersion optic (Nikon, CFI PlanFluor, NA 1.49) and NIS Elements Software. The sample was excited using the 470 nm line of a Lumencor diode-pumped light engine (SpectraX, Lumencor Inc., Beaverton OR). Fluorescence was detected using an ET-GFP filter set (Chroma Technology Corp) and ORCA-Flash 4.0 sCMOS camera (HAMAMATSU Corporation, Bridgewater, NJ). Within 30 s, a significant increase in fluorescence was observed in HeLa cells (FIG. 24A). Punctate fluorescence in cytoplasm suggested that 1 might localize within mitochondria.

Figure 24B:
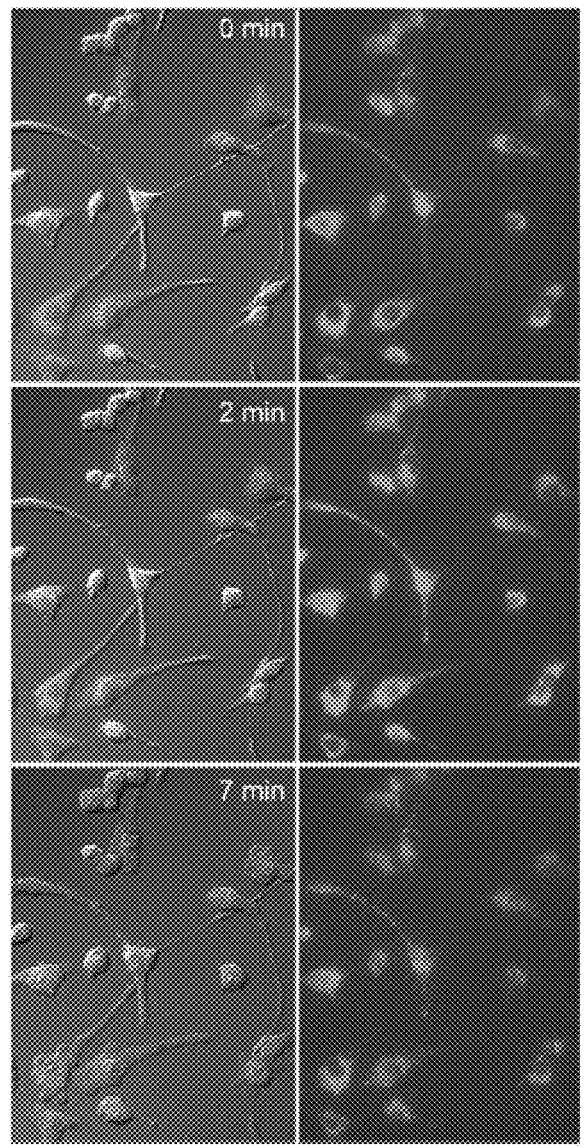
Figure 24C:
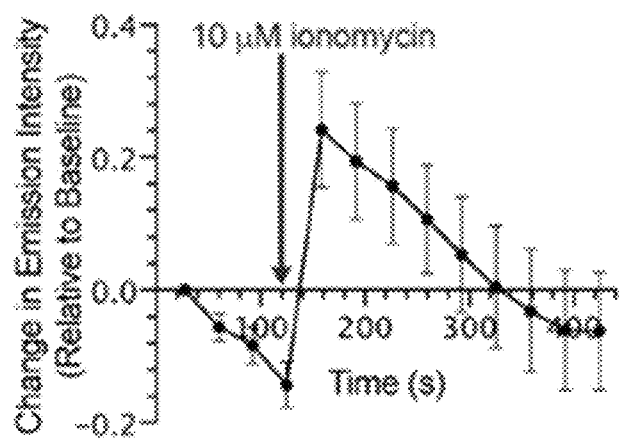
Figure 25A:
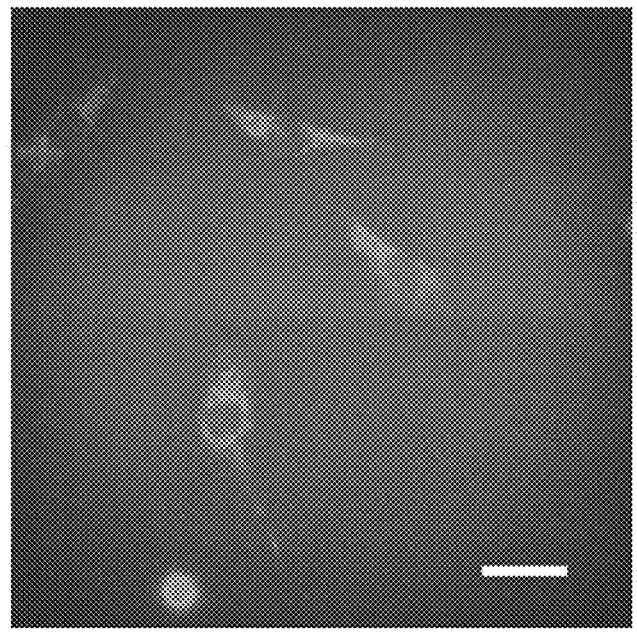
FIGS. 25A-B. Pseudo-color image of RAW cells loaded with 5 μM dihydrodichlorofluorescein diacetate (A) without stimulation by ionomycin and (B) with stimulation by ionomycin. Scale bars are 20 μm.
Figure 25B:
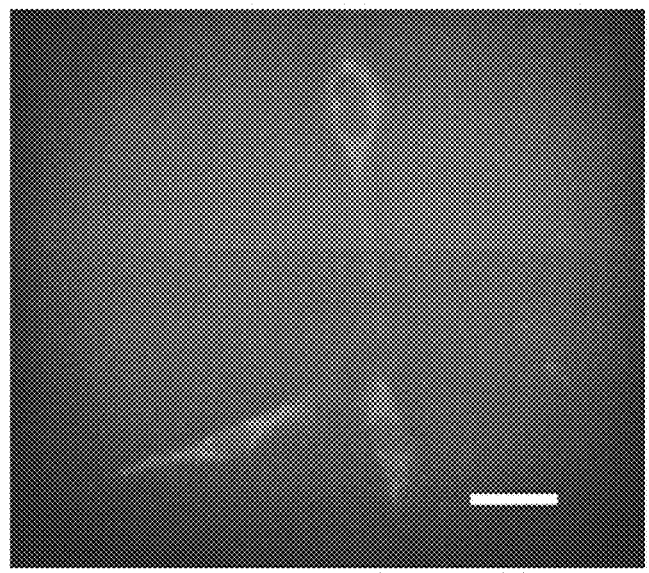

After detecting exogenously added $H_2O_2$ in cells, the focus shifted to more biologically relevant, endogenous $H_2O_2$. It was attempted to monitor endogenous $H_2O_2$ production upon stimulation with ionomycin in RAW cells. When ionomycin was added in the presence of the most widely used fluorescent probe for ROS, dihydrodichlorofluorescein acetate, fluorescence increase could hardly be observed (FIGS. 25A-B). In contrast, with probe 1, a significant response was observed within 30 s after the addition of ionomycin relative to the baseline fluorescence (FIG. 24B-C) and peaked at 48 s. Therefore, not only did this experiment show the superiority with probe 1, the kinetics of pharmacological $H_2O_2$ production was found to be much faster than previously thought.

Figure 24D:
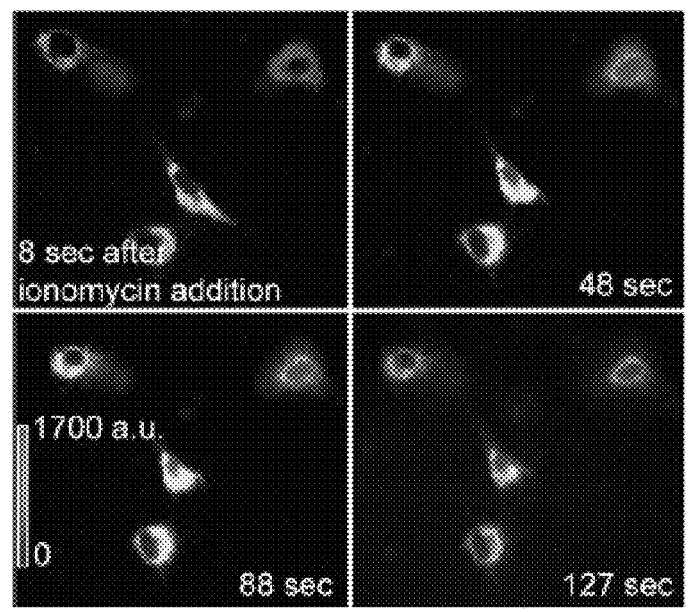

To study the localization of 1, endothelial cells were simultaneously incubated with 1 µM MitoTracker® Red FM (ThermoFisher Scientific) for 20 min at 37° C. (FIG. 24D). The dish was inserted in a closed, thermo-controlled (37° C.) stage top incubator (Tokai Hit Co., Shizuoka-ken, Ja-pan) atop the motorized stage of an inverted Nikon TiE fluorescent microscope (Nikon Inc., Melville, NY) equipped with a 60× oil immersion optic (Nikon, CFI PlanFluor, NA 1.49) and NIS Elements Software. The sample was excited using the 555 nm line and detected using a TRITC filter set. The first image taken 8 s after the addition of ionomycin already showed increased fluorescence, and time-lapse imaging showed that fluorescence continued to increase over time. The overlap of the green and red fluorescence indicated that the probe might be localizing to mitochondria. However, the Pearson correlation coefficient was 0.114±0.034, suggesting that although some overlap with mitochondria was observed, the bulk of the green fluorescence was observed outside of mitochondria. Furthermore, the diffusion of both the green and red fluorescence indicated that stimulation with ionomycin likely induced changes in mitochondrial membrane potential or permeability causing the contents to leak out.

$H_2O_2$ has been recognized as a critical signaling molecule for the recruitment of immune cells for wound regeneration. To date, only genetically encoded protein-based fluorescent probes have been able to illuminate the spatiotemporal dynamics of $H_2O_2$ for wound healing models in zebrafish. It was hypothesized that our method might be rapid enough to match the protein-based imaging in vivo. As a platform to test this hypothesis, 1 was applied to image a zebrafish tail wound-healing model.

Three-day post-fertilization zebrafish embryos were removed from their chorion and allowed to swim in 1 mM 1 for 2 h (0.1% v/v DMSO), leading to effective dye loading. Following this, the fish were anesthetized and mounted in agar. The tail fins were clipped with a razor blade. Fluorescence images were obtained every 60 s for 60 min using an inverted Nikon TiE fluorescent microscope (Nikon Inc., Melville, NY) equipped with a 20× 0.75 NA lens and NIS Elements Software. The sample was excited using the 470 nm line of a Lumencor diode-pumped light engine (SpectraX, Lumencor Inc., Beaverton OR), and the fluorescence signals were detected using an ET-GFP filter set (Chroma Technology Corp) and ORCA-Flash 4.0 sCMOS camera (HAMAMATSU Corporation, Bridgewater, NJ).

Figure 26A:
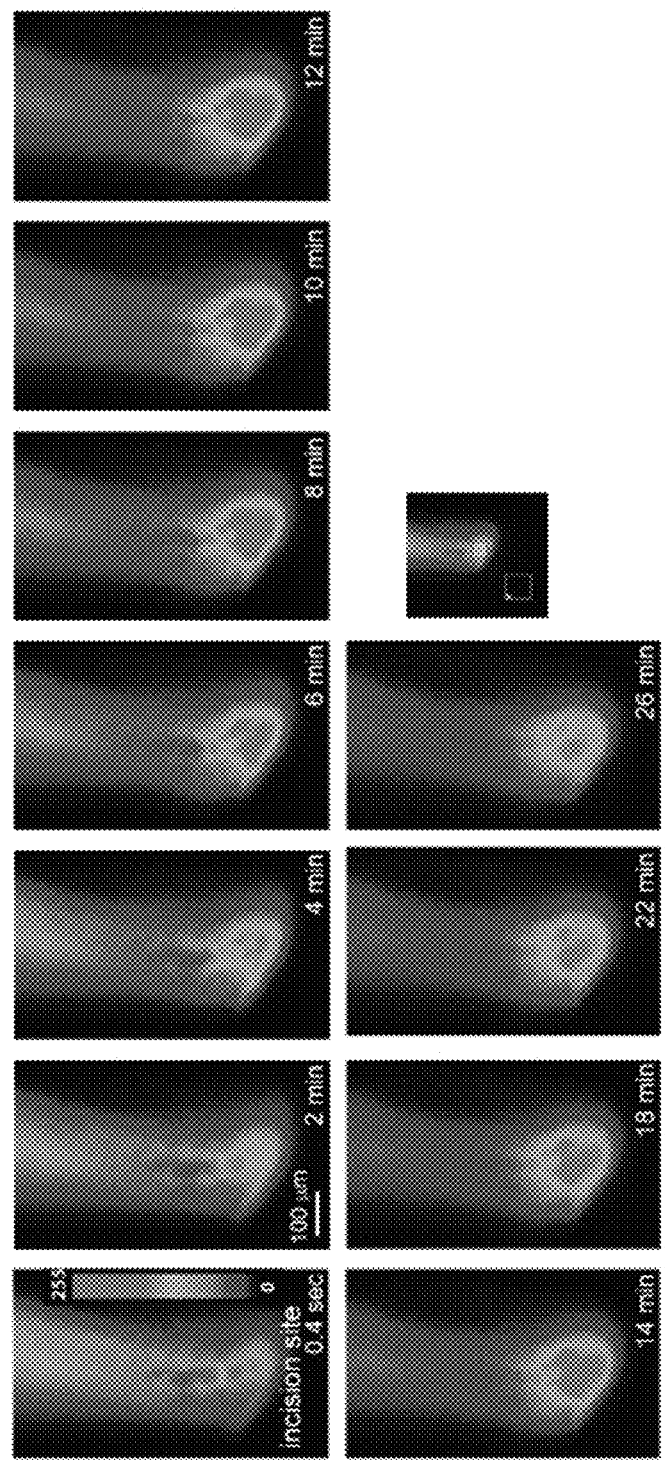
FIGS. 26A-B. Imaging of $H_2O_2$ in zebrafish wound-healing model. A) Snap shots of the fluorescence imaging of wound-induced $H_2O_2$. Zebrafish were loaded with 1, then had the tails snipped. $H_2O_2$ was produced at the incision site over the course of 30 min. B) The fluorescence intensity over time. The Y-axis=fluorescence intensity in the red square—fluorescence intensity in the green square.
Figure 26B:
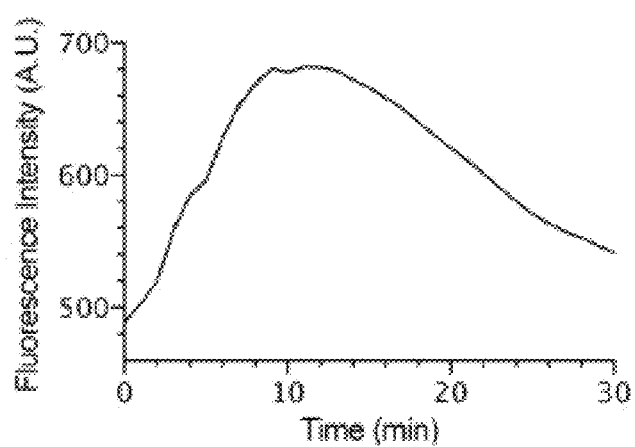

An increase in fluorescence intensity was observed, with the fluorescence at a maximum approximately 10-20 min after tail snipping. As shown in FIGS. 26A-B, the probe 1 was capable of providing the spatiotemporal information for the tail samples.

In conclusion, the reaction of the nonfluorescent selenide 1 with $H_2O_2$ forms the fluorescent phenol 5 via the oxidation/[2,3]-sigmatropic rearrangement/hydrolysis sequence. Selenide 1 reacts with $H_2O_2$ seven times faster than boronate-based probes. The second-order rate constant for the reaction of 1 with $H_2O_2$ was of the same order of magnitude as the reaction of thiols with $H_2O_2$, indicating that the detection of intracellular $H_2O_2$ is not severely hampered by endogenous thiols. This is consistent with the notion that the oxidation of selenium is faster than that of sulfur compounds. The careful control experiments ensured that the intended ROS was monitored. Selenide 1 was found to be selective for $H_2O_2$.

Selenide 1 instantaneously responded to both exogenously applied and endogenously produced $H_2O_2$, indicating its applicability in gaining spatiotemporal insights into cellular pathways involving $H_2O_2$. Ionomycin is a widely used reagent to intracellularly induce $H_2O_2$ in approximately 2 min. It was discovered that $H_2O_2$ was produced earlier (8-48 s) with ionomycin. Generally, chemical probes for $H_2O_2$ detect endogenously produced $H_2O_2$ later times (ca. 30 min). In the zebrafish tail wounding model, the rapid generation of $H_2O_2$ near the wound site was observed in real time using selenide 1, recapitulating the results using a protein-based probe.

It is acknowledged that two challenges exist with 1. First, the fluorophore 5 diffuses throughout the cell, complicating studies that require extended time periods. Second, the pKa of 5 is ≈7 and, thus, the fluorescence signals are weakened under acidic conditions. Nonetheless, the use of seleno Mislow-Evans rearrangement provides a new platform for fluorometric detection of intracellular $H_2O_2$.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

The invention claimed is:

1. A compound having the structure:

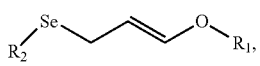

wherein:
R₁ is a fluorescent dye moiety that does not fluoresce when incorporated in the compound or fluoresces with a different intensity or peak wavelength when incorporated in the compound; and
R₂ is optionally substituted and is alkyl, heteroalkyl, aryl, heteroaryl, or any combination of the proceeding.

2. The compound of claim 1, wherein R₁ is a xanthene dye moiety, and R₂ is phenyl, optionally substituted aryl, optionally substituted heteroaryl, or $C_1$-$C_{10}$ alkyl.

3. The compound of claim 2, wherein R₁ is

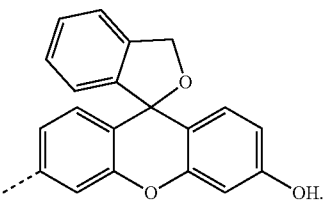

4. The compound of claim 2, wherein R₁ is

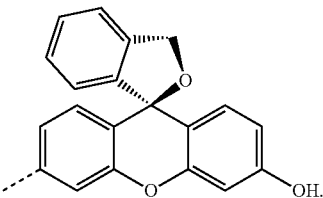

5. The compound of claim 2, wherein R₂ is phenyl.

6. The compound of claim 2, wherein R₂ is a nitrogen-substituted heteroaryl moiety.

7. The compound of claim 6, wherein R₂ is a pyridine moiety.

8. The compound of claim 6, wherein R₂ is

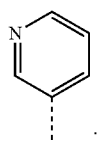

9. The compound of claim 1 having the structure:

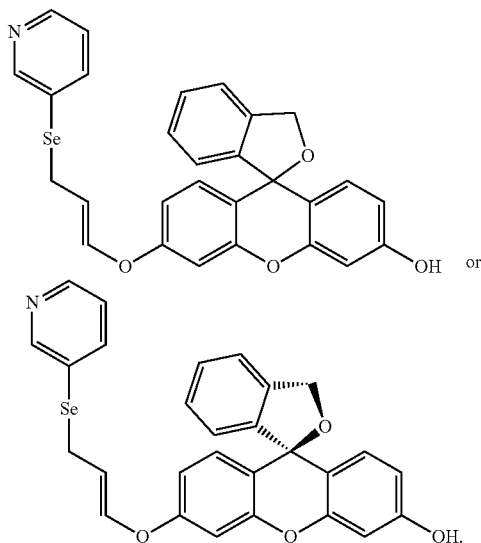

10. The compound of claim 1 having the structure:

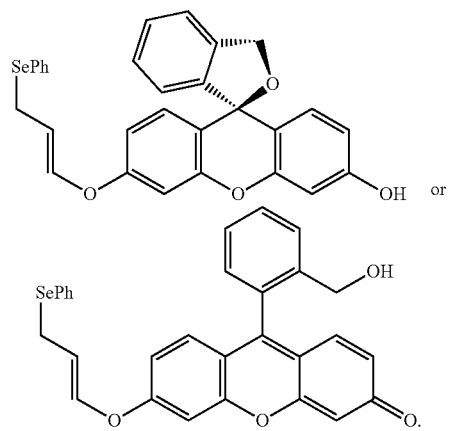

11. A method of identifying or visualizing the presence of $H_2O_2$ in a cell, tissue, organ, or organism, comprising contacting the cell, tissue, organ, or organism with a compound according to claim 1, illuminating the cell, tissue, organ, or organism with light including or at an excitation wavelength for the reaction product of the compound with $H_2O_2$, and detecting fluorescent emission from the reaction product.

12. The method of claim 11, further comprising obtaining an image of the cell, tissue, organ, or organism at or including light at the excitation wavelength for the reaction product of the compound with $H_2O_2$, optionally using fluorescence microscopy.

13. The method of claim 11, further comprising obtaining a spectrograph of light emitted by the reaction product, and optionally quantifying $H_2O_2$ based on light emitted by the reaction product.

14. The method of claim 11, further comprising sorting cells using a fluorescence-activated cell sorter, based on an amount of light emitted by the reaction product in each cell.

15. The method of claim 14, further comprising classifying cells sorted based on the amount of light emitted by the reaction product in each cell, and quantifying $H_2O_2$ production in the sorted cells based on the number of cells sorted.

16. A method of identifying or quantifying the presence of $H_2O_2$ in a sample, comprising adding to or mixing in the sample a compound according to claim 1, illuminating the sample with light including or at an excitation wavelength for the reaction product of the compound with $H_2O_2$, and detecting fluorescent emission from the reaction product.

17. The method of claim 16, wherein the sample is contained within a cuvette, multi-well plate, or lateral flow device, optionally wherein the cuvette, multi-well plate, or lateral flow device are disposable, or form part of a disposable article.

18. The method of claim 16, wherein the sample is a biological sample, such as blood, plasma, serum, urine, cerebrospinal fluid, mucus, lymph, cell lysate or a fraction or derivative thereof, or conditioned cell culture medium.

19. The method of claim 16, wherein the $H_2O_2$ is converted to a different compound in an enzyme-linked immunoassay, e.g., using catalase to decompose the $H_2O_2$ to water and oxygen, and the identification or quantification of the presence of the $H_2O_2$ measures the presence of or quantity of an analyte or binding activity detected by the immunoassay.

\* \* \* \* \*